United States Patent
Glombik et al.

(10) Patent No.: US 7,538,131 B2
(45) Date of Patent: May 26, 2009

(54) 2-{-3-'2-(PHENYL)-OXAZOL-4-YLMETHOXYMETHYL-CYCLOHEXYLMETHOXY}-PROPIONIC ACID DERIVATIVES USEFUL AS PEROXISOME PROLIFERATOR-ACTIVATED RECEPTOR (PPAR) LIGANDS FOR THE TREATMENT OF HYPERLIPIDEMIA AND DIABETES

(75) Inventors: Heiner Glombik, Hofheim (DE); Christian Stapper, Mainz (DE); Eugen Falk, Frankfurt (DE); Stefanie Keil, Hofheim (DE); Hans-Ludwig Schaefer, Hochheim (DE); Wolfgang Wendler, Selters (DE); Stephanie Knieps, Sulzbach (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 11/670,594

(22) Filed: Feb. 2, 2007

(65) Prior Publication Data

US 2007/0197612 A1   Aug. 23, 2007

Related U.S. Application Data

(63) Continuation of application No. PCT/EP2005/008284, filed on Jul. 30, 2005.

(30) Foreign Application Priority Data

Aug. 14, 2004 (DE) .................... 10 2004 039 533

(51) Int. Cl.
A61K 31/42 (2006.01)
C07D 263/30 (2006.01)
(52) U.S. Cl. ....................... 514/374; 548/235
(58) Field of Classification Search ............... None
See application file for complete search history.

(56) References Cited

FOREIGN PATENT DOCUMENTS

WO     WO 03/020269     3/2003
WO     WO 2004/076427   9/2004

*Primary Examiner*—Paul A Zucker
(74) *Attorney, Agent, or Firm*—Jiang Lin; Craig M. Bell

(57) ABSTRACT

The present invention comprises compounds and compositions for the treatment of metabolic disorders and more particularly, those insulin-related metabolic disorders of the blood such as hyperlipidemia, diabetes, insulin-resistance and the like comprising acetic acid derivatives with cyclohexylmethoxy substituents and their salts. Known as peroxisome proliferator-activated receptors (PPAR) agonists/antagonists, the invention relates to compounds of the formula I

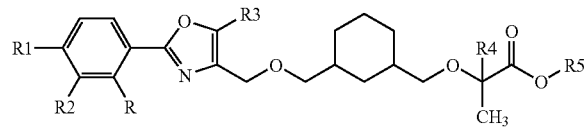

I wherein the various substituent R-groups are more specifically defined herein.

8 Claims, No Drawings

2-{-3-'2-(PHENYL)-OXAZOL-4-YLMETHOXYMETHYL-CYCLOHEXYLMETHOXY}-PROPIONIC ACID DERIVATIVES USEFUL AS PEROXISOME PROLIFERATOR-ACTIVATED RECEPTOR (PPAR) LIGANDS FOR THE TREATMENT OF HYPERLIPIDEMIA AND DIABETES

CROSS-REFERENCE TO RELATED APPLICATIONS

This application is a continuation of International Patent Application No. PCT/EP2005/008284 filed on Jul. 30, 2005 which is incorporated herein by reference in its' entirety which also claims the benefit of priority of German Patent Application No. 10/2004 039533.0 filed on Aug. 14, 2004.

FIELD OF THE INVENTION

The invention relates generally to compounds and compositions for the treatment of metabolic disorders and more particularly, those insulin-related metabolic disorders of the blood such as hyperlipidemia and diabetes and the like. More specifically, the present invention relates to compounds that therapeutically modulation and control lipid and/or carbohydrate metabolism and are thus suitable for the prevention and/or treatment of diseases such as type 2 diabetes and atherosclerosis, and the diverse manifestations thereof. Even more specifically, the present invention relates to acetic acid derivatives with cyclohexylmethoxy substituents, their salts and functional derivatives thereof as well as methods for their preparation and formulation as pharmaceutical compositions for the treatment of said disorders.

BACKGROUND OF THE INVENTION

Compounds comprising structures similar to the acetic acid derivatives with cyclohexylmethoxy substituents and their salts as described herein are known and have also been described in the art for the treatment of hyperlipidemia and diabetes (see WO 2004/076427 to Stapper et. al.).

The compounds of the present invention are highly effective in the therapeutic modulation of lipid and/or carbohydrate metabolism and are therefore useful in the prevention and/or treatment of diseases such as type-2 diabetes and atherosclerosis, and the many other diverse cardiovascular, among others, manifestations therefrom. These compounds have been found to exhibit peroxisome proliferator-activated receptor (PPAR) agonist/antagonist activity, in particular, an excellent PPARalpha modulatory effect as well as a correspondingly excellent PPARgamma modulatory effect.

The peroxisome proliferator-activated receptors (PPAR) are transducer proteins belonging to the steroid/thyroid/retinoid receptor superfamily. The PPAR receptors were originally identified as orphan receptors without known ligands, but were known for their ability to mediate the pleiotropic effects of fatty acid peroxisome proliferators. These receptors function as ligand-regulated transcription factors that control the expression of target genes by binding to their responsive DNA sequences as heterodimers with RXR. The target genes encode enzymes involved in a number of metabolic and cell growth/cell proliferation/cell differentiation inductions. These then provide targets for the development of therapeutic agents for the treatment of metabolic and central nervous system disorders, among others.

PPAR agonists are well known and have been described in the prior art, see U.S. Pat. No. 6,200,995 to De La Brouse-Elwood et. al.; WO 03/043997 to Johnston et. al. and WO 01/00603 and WO 02/092590 to Keil et. al. ). comprising an oxadiazolone feature as inhibitors of factor Xa were disclosed in DE 101 12 768 A1 and oxodiazolones have also been described as oral hypoglycemic agents in WO 96/13264.

SUMMARY OF THE INVENTION

The present invention comprises compounds and compositions for the treatment of metabolic disorders and more particularly, those insulin-related metabolic disorders of the blood such as hyperlipidemia, diabetes, insulin-resistance and the like comprising acetic acid derivatives with cyclohexylmethoxy substituents and their salts. Known as peroxisome proliferator-activated receptors (PPAR) agonists/antagonists, the invention relates to compounds of the formula I

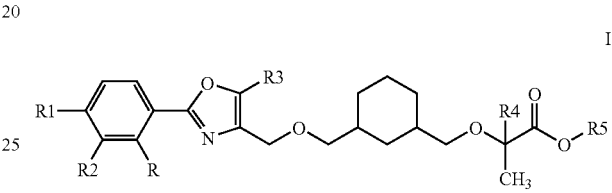

wherein the various substituent R-groups are more specifically defined herein.

DETAILED DESCRIPTION OF THE INVENTION

The present invention comprises compounds and compositions for the treatment of metabolic disorders and more particularly, those insulin-related metabolic disorders of the blood such as hyperlipidemia and diabetes and the like comprising acetic acid derivatives with cyclohexylmethoxy substituents and their salts. Known as peroxisome proliferator-activated receptors (PPAR) agonists/antagonists, the invention relates to compounds of the formula I

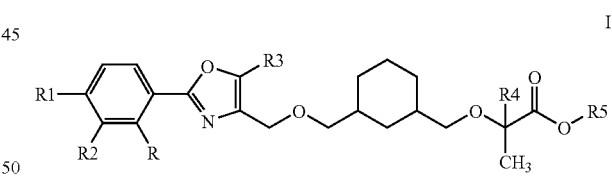

in which the meanings of the respective R-groups are as follows:

R is selected from the group consisting of H and $CF_3$;

R1 is selected from the group consisting of H, $CF_3$, (C1-C6)-alkyl, phenyl and, phenoxy;

R2 is selected from the group consisting of H, (C1-C4)-alkyl, O—(C1-C4)-alkyl, $CF_3$; and when R1 and R2 are fused together with the phenyl ring they form naphthyl;

R3 is selected from the group consisting of (C1-C6)-alkyl;

R4 is selected from the group consisting of (C1-C6)-alkyl, benzyl;

R5 is selected from the group consisting of H, (C1-C6)-alkyl;

as well as their suitable salts, solvates and derivatives thereof.

Preferred compounds of formula I above are those in which
R is H;
R1 is selected from the group consisting of H, methyl, butyl, phenyl, phenoxy and $CF_3$;
R2 is selected from the group consisting of H, methyl, methoxy and $CF_3$;
and when R1 and R2 are fused together with the phenyl ring they form naphthyl;
R3 selected from the group consisting of ethyl or propyl;
R4 is methyl; and
R5 is H.

The alkyl groups comprising the substituents R, R1, R2, R3, R4 and R5 may be either straight-chain or branched.

The compounds of the formula I comprise at least two centers of asymmetry and may optionally comprise more in addition thereto. The compounds of the formula I may therefore be in the form of their racemates, racemic mixtures, pure enantiomers, diastereomers and diastereomeric mixtures. The present invention includes all these isomeric forms of the compounds of the formula I. These isomeric forms can be obtained and isolated if necessary by well known methods in the art.

Pharmaceutically acceptable salts of the claimed compounds are particularly suitable for medical applications because their solubility in water is greater than that of the initial or basic compounds. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), trometamol(2-amino-2-hydroxymethyl-1,3-propanediol), diethanolamine, lysine or ethylenediamine.

Even those salts with a pharmaceutically unacceptable anion such as, for example, trifluoroacetate, however, also fall within the scope of the present invention since these may also be useful intermediates for the preparation or purification of pharmaceutically acceptable salts and/or for use in non-therapeutic in vitro applications.

The term "physiologically functional derivative" as used herein refers to any physiologically suitable derivative of a compound of formula I of the invention, such as an ester, which on administration to a mammal such as a human is able to form (directly or indirectly) a compound of the formula I or an active metabolite thereof.

Physiologically functional derivatives also include prodrugs of the compounds of the invention, as described, for example, in H. Okada et al., Chem. Pharm. Bull. 1994, 42, 57-61. Such pro-drugs can be metabolized in vivo to a compound of the invention. These pro-drugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of formula I as described above, their salts, solvates and physiologically functional derivatives as described herein.

This invention further relates to the use of the compounds of the formula I and their pharmaceutical compositions as peroxisome proliferator-activated receptor (PPAR) receptor ligands. The PPAR receptor ligands of the invention are suitable as modulators of PPAR receptor activity.

As discussed briefly earlier, peroxisome proliferator-activated receptors (PPAR) are transcription factors which can be activated by ligands and belong to the class of nuclear hormone receptors. There are three PPAR isoforms, PPARalpha, PPARgamma and PPARdelta, which are encoded by different genes (see *Peroxisome Proliferator-Activated Receptor (PPAR): Structure, Mechanisms of Activation and Diverse Functions:* Motojima K, Cell Struct Funct., Oct, 18, 1993(5), 267-77). Which is hereby incorporated by reference.

Two variants of PPARgamma exist, $PPARgamma_1$ and $gamma_2$, which are the result of an alternative use of the promoters and differential mRNA splicing (Vidal-Puig et al. J. Clin. Invest., 97:2553-2561, 1996). Different PPAR receptors have different tissue distribution and modulate different physiological functions. The PPAR receptors play a key role in various aspects of the regulation of a large number of genes, the products of which genes are directly or indirectly crucially involved in lipid and carbohydrate metabolism. Thus, for example, PPARalpha receptors play an important part in the regulation of fatty acid catabolism or lipoprotein metabolism in the liver, while PPARgamma is crucially involved for example in regulating adipose cell differentiation. In addition, however, PPAR receptors are also involved in the regulation of many other physiological processes, including those which are not directly connected with carbohydrate or lipid metabolism. The activity of different PPAR receptors can be modulated by various fatty acids, fatty acid derivatives and synthetic compounds to varying extents. For relevant reviews about functions, physiological effect and pathophysiology, see: Joel Berger et al., Annu. Rev. Med., 2002, 53, 409-435; Timothy Wilson et al., J. Med. Chem., 2000, Vol. 43, No. 4, 527-550; Steven Kliewer et al., Recent Prog Horm Res., 2001, 56, 239-63.

The present invention relates to compounds of the formula I suitable for modulating the activity of PPAR receptors, especially the activity of PPARalpha and PPARgamma. Depending on the modulation profile, the compounds of the formula I are suitable for the treatment, control and prophylaxis of the indications described hereinafter, and for a number of other pharmaceutical applications connected thereto (see, for example, Joel Berger et al., Annu. Rev. Med., 2002, 53, 409-435; Timothy Wilson et al. J. Med. Chem., 2000, Vol. 43, No. 4, 527-550; Steven Kliewer et al., Recent Prog Horm Res. 2001; 56: 239-63; Jean-Charles Fruchart, Bart Staels and Patrick Duriez: PPARS, Metabolic Disease and Arteriosclerosis, Pharmacological Research, Vol. 44, No. 5, 2001; Sander Kersten, Beatrice Desvergne & Walter Wahli: Roles of PPARs in health and disease, NATURE, VOL 405, 25 May 2000; Ines Pineda Torra, Giulia Chinetti, Caroline Duval, Jean-Charles Fruchart and Bart Staels: Peroxisome proliferator-activated receptors: from transcriptional control to clinical practice, Curr Opin Lipidol 12: 2001, 245-254).

Compounds of this type are particularly suitable for the treatment and/or prevention of Disorders of fatty acid metabolism and glucose utilization disorders Disorders in which insulin resistance is involved Diabetes mellitus, especially type-2 diabetes, including the prevention of the disease manifestations associated therewith.

Particular metabolic states/results achievable by treatment using compounds/compositions of the present invention include, but are not limited to:
- hyperglycemia,
- improvement in insulin resistance,
- improvement in glucose tolerance,
- protection of the pancreatic β cells
- prevention of macro- and microvascular disorders Other metabolic disorders and their associated disease states suitable for the treatment and/or prevention resulting therefrom include:

A. Dyslipidemias and the disease states resulting therefrom such as, for example, atherosclerosis, coronary heart disease, cerebrovascular disorders etc, especially those (but not restricted thereto) which are characterized by one or more of the following factors:
- high plasma triglyceride concentrations, high postprandial plasma triglyceride concentrations,
- low HDL cholesterol concentration
- low ApoA lipoprotein concentrations
- high LDL cholesterol concentrations
- small dense LDL cholesterol particles
- high ApoB lipoprotein concentrations B. Various other conditions which may be associated with the metabolic syndrome, such as:
- obesity (excess weight), including central obesity
- thromboses, hypercoagulable and prothrombotic stages (arterial and venous)
- high blood pressure
- heart failure such as, for example (but not restricted thereto), following myocardial infarction, hypertensive heart disease or cardiomyopathy C. Further disorders or conditions in which for example inflammatory reactions or cell differentiation are involved:
- atherosclerosis such as, for example (but not restricted thereto), coronary sclerosis including angina pectoris or myocardial infarction, stroke
- vascular restenosis or re-occlusion
- chronic inflammatory bowel diseases such as, for example, Crohn's disease and ulcerative colitis
- pancreatitis
- other inflammatory states
- retinopathy
- adipose cell tumors
- lipomatous carcinomas such as, for example, liposarcomas
- solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc.
- acute and chronic myeloproliferative disorders and lymphomas
- angiogenesis
- neurodegenerative disorders
- Alzheimer's disease
- multiple sclerosis
- Parkinson's disease
- erythemato-squamous dermatoses such as, for example, psoriasis
- acne vulgaris
- other skin disorders and dermatological conditions which are modulated by PPAR
- eczemas and neurodermatitis
- dermatitis such as, for example, seborrheic dermatitis or photodermatitis
- keratitis and keratoses such as, for example, seborrheic keratoses, senile keratoses, actinic keratosis, photo-induced keratoses or keratosis follicularis
- keloids and keloid prophylaxis
- warts, including condylomata or condylomata acuminata
- human papilloma viral (HPV) infections such as, for example, venereal warts, viral warts such as, for example, molluscum contagiosum, leukoplakia
- papular dermatoses such as, for example, lichen planus
- skin cancer such as, for example, basal-cell carcinomas, melanomas or cutaneous T-cell lymphomas
- localized benign epidermal tumors such as, for example, keratoderma, epidermal naevi
- chilblains
- high blood pressure
- syndrome X
- polycystic ovary syndrome (PCOS)
- asthma
- osteoarthritis
- lupus erythematosus (LE) or inflammatory rheumatic disorders such as, for example, rheumatoid arthritis
- vasculitis
- wasting (cachexia)
- gout
- ischemia/reperfusion syndrome
- acute respiratory distress syndrome (ARDS)

The amount of a compound of formula I necessary to achieve the desired biological effect depends on a number of factors, for example, the specific compound chosen, the intended use, the mode of administration and the clinical condition of the patient. The daily dose is generally in the range from 0.001 mg to 100 mg (typically of 0.01 mg and 50 mg) per day and per kilogram of bodyweight, for example 0.1-10 mg/kg/day. An intravenous dose may be, for example, in the range from 0.001 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, capsules or tablets, may contain, for example, from 0.05 to 1000 mg, typically from 0.5 to 600 mg. For the therapy of the above-mentioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful to the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral, i.e., sublingual and parenteral i.e., subcutaneous, intramuscular, intradermal or intravenous, administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate (PVA) phthalate, hydroxypropyl methylcellulose (HPMC) phthalate and anionic polymers of methacrylic acid and methyl methacrylate.

Suitable pharmaceutical preparations for oral administration may be in the form of separate units such as, for example, capsules, cachets, slow-dissolving oral tablets, each of which contain a defined amount of the compound of formula I; as powders or granules, as solution or suspension in an aqueous or non-aqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agents in a suitable machine. Molded tablets can be produced by molding the compound, which is in powder form and is moistened with an inert liquid diluent, in a suitable machine.

Pharmaceutical compositions which are suitable for peroral (sublingual) administration comprise slow-dissolving, oral tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5.0% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electro-transport or iontophoresis as described, for example, in Pharmaceutical Research, 2(6): 318 (1986) which is also hereby incorporated by reference.

The compounds of the formula I are distinguished by favorable effects on metabolic disorders. They beneficially influence lipid and sugar metabolism, in particular they lower the triglyceride level and are suitable for the prevention and treatment of type 11 diabetes and arteriosclerosis and the diverse disease conditions which are a result thereof.

The compounds of the present invention according to formula I can be administered alone or optionally in combination with one or more secondary pharmacologically active substances which are effective in the treatment of metabolic disturbances or disorders frequently associated therewith. Examples of such additional active compounds are:

1. active compounds which lower blood glucose, i.e., anti-diabetic agents,
2. active ingredients for the treatment of dyslipidemias,
3. anti-atherosclerotic compounds anti-obesity agents,
4. anti-inflammatory active compounds
5. active compounds for the treatment of malignant tumors
6. anti-thrombotic active compounds
7. active compounds for the treatment of high blood pressure
8. active compounds for the treatment of heart failure and
9. active compounds for the treatment and/or prevention of complications caused by diabetes or associated with diabetes.

These compounds can be combined with the compounds of the invention of formula I resulting in a synergistic enhancement or improvement in the therapeutic effect. Administration of the active ingredient combination can take place either by separate administration of the active ingredients to the patient or in the form of combination products in which a plurality of active ingredients are present in one pharmaceutical preparation. Specific examples of the additional active compounds suitable for combination with those of the present invention include, but are not limited to:

1. Anti-diabetic Agents

Suitable antidiabetic agents are disclosed in the Rote Liste 2001, chapter 12 or in the USP Dictionary of USAN and International Drug Names, US Pharmacopeia, Rockville 2003. Suitable antidiabetic agents include all insulins and insulin derivatives such as, for example, Lantus® (see www-.lantus.com) or Apidra®, and other fast-acting insulins (see U.S. Pat. No. 6,221,633 to Ertle et. al.), GLP-1 receptor modulators as described in WO 01/04146 or else, for example, those disclosed in U.S. Pat. No. 6,268,343 to Knudsen et. al. (Novo Nordisk A/S) both of which are incorporated by reference herein The orally effective hypoglycemic active ingredients include, preferably, sulfonylureas, biguanidines, meglitinides, oxadiazolidinediones, thiazolidinediones, glucosidase inhibitors, glucagon antagonists, oral GLP-1 agonists, DPP-IV inhibitors, potassium channel openers such as, for example, those disclosed in U.S. Pat. No 5,889,002 and U.S. Pat. No. 6,225,310 both to Nielsen et. al., insulin sensitizers, inhibitors of liver enzymes involved in the stimulation of gluconeogenesis and/or glycogenolysis, modulators of glucose uptake, compounds which alter lipid metabolism and lead to a change in the blood lipid composition, compounds which reduce food intake or food absorption, PPAR and PXR modulators and active ingredients which act on the ATP-dependent potassium channel of the beta cells.

In one embodiment of the invention, the compounds of the formula I are administered in combination with insulin.

In one embodiment of the invention, the compounds of the formula I are in combination with substances which influence hepatic glucose production such as, for example, glycogen phosphorylase inhibitors (see: WO 01/94300, WO 02/096864, WO 03/084923, WO 03/084922, WO 03/104188).

In another embodiment, the compounds of the formula I are administered in combination with a sulfonylurea such as, for example, tolbutamide, glibenclamide, glipizide or glimepiride.

In a third embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In yet another embodiment, the compounds of the formula I are administered in combination with a biguanide such as, for example, metformin.

In a further embodiment, the compounds of the formula I are administered in combination with a meglitinide such as, for example, repaglinide.

The compounds of the formula I may also be administered in combination with a thiazolidinedione such as, for example, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In another embodiment, the compounds of the formula I are in combination with a dipeptidyl peptidase IV (DPP-IV) inhibitor as described, for example, in WO 98/19998, WO99/61431, WO99/67278, WO99/67279, WO01/72290, WO 02/38541, WO03/040174, in particular P 93/01 (1-cyclopentyl-3-methyl-1-oxo-2-pentanammonium chloride), P-31/98, LAF237 (1-[2-[3-hydroxyadamant-1-ylamino)acetyl]pyrrolidine-2-(S)-carbonitrile), TS021 ((2S, 4S)-4-fluoro-1-[[(2-hydroxy-1,1-dimethylethyl)amino]acetyl]pyrrolidine-2-carbonitrile monobenzenesulfonate).

In one embodiment of the invention, the compounds of the formula I are administered in combination with a PPAR-gamma agonist such as, for example, rosiglitazone or pioglitazone.

In one embodiment, the compounds of the formula I are administered in combination with compounds with an inhibitory effect on SGLT-1 and/or 2, as disclosed directly or indirectly for example in WO 2004/007517, WO 2004/052902 and WO 2004/052903.

In another embodiment, the compounds of the formula I are administered in combination with an a-glucosidase inhibitor such as, for example, miglitol or acarbose.

In one embodiment, the compounds of the formula I are administered in combination with more than one of the aforementioned compounds, e.g. in combination with a sulfonylurea and mefformin, a sulfonylurea and acarbose, repaglinide and metformin, insulin and a sulfonylurea, insulin and metformin, insulin and troglitazone, insulin and lovastatin, etc.

Lipid Modulators

In one embodiment of the invention, the compounds of the formula I are administered in combination with an HMGCoA reductase inhibitor such as lovastatin, fluvastatin, pravastatin, simvastatin, ivastatin, itavastatin, atorvastatin, rosuvastatin.

In one embodiment of the invention, the compounds of the formula I are administered in combination with a bile acid absorption inhibitor (see, for example, U.S. Pat. Nos. 6,245, 744; 6,221,897 and 6,277,831 all to Frick et al, EP 0683 773, EP 0683 774).

In one embodiment of the invention, the compounds of the formula I are administered in combination with a polymeric bile acid adsorbent such as, for example, cholestyramine, colesevelam.

In one embodiment of the invention, the compounds of the formula I are administered in combination with a cholesterol absorption inhibitor as described for example in WO 0250027, or ezetimibe, tiqueside, pamaqueside.

In one embodiment of the invention, the compounds of the formula I are administered in combination with an LDL receptor inducer (see, for example, U.S. Pat. No. 6,342,512).

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (September-October 2001), 18(5), 230-6). Caromax is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

In one embodiment of the invention, the compounds of the formula I are administered in combination with a PPARalpha agonist.

In one embodiment of the invention, the compounds of the formula I are administered in combination with a mixed PPAR alpha/gamma agonist such as, for example, AZ 242 (Tesaglitazar, (S)-3-(4-[2-(4-methanesulfonyloxyphenyl) ethoxy]phenyl)-2-ethoxypropionic acid), BMS 298585 (N-[(4-methoxyphenoxy)carbonyl]-N-[[4-[2-(5-methyl-2-phenyl-4-oxazolyl)ethoxy]phenyl]methyl]glycine) or as described in WO 99/62872, WO 99/62871, WO 01/40171, WO 01/40169, WO96/38428, WO 01/81327, WO 01/21602, WO 03/020269, WO 00/64888 or WO 00/64876.

In one embodiment of the invention, the compounds of the formula I are administered in combination with a fibrate such as, for example, fenofibrate, gemfibrozil, clofibrate, bezafibrate.

In one embodiment of the invention, the compounds of the formula I are administered in combination with nicotinic acid or niacin.

In one embodiment of the invention, the compounds of the formula I are administered in combination with a CETP inhibitor, e.g. CP-529, 414 (torcetrapib).

In one embodiment of the invention, the compounds of the formula I are administered in combination with an ACAT inhibitor.

In one embodiment of the invention, the compounds of the formula I are administered in combination with an MTP inhibitor such as, for example, implitapide.

In one embodiment of the invention, the compounds of the formula I are administered in combination with an antioxidant.

In one embodiment of the invention, the compounds of the formula I are administered in combination with a lipoprotein lipase inhibitor.

In one embodiment of the invention, the compounds of the formula I are administered in combination with an ATP citrate lyase inhibitor.

In one embodiment of the invention, the compounds of the formula I are administered in combination with a squalene synthetase inhibitor.

In one embodiment of the invention, the compounds of the formula I are administered in combination with a lipoprotein (a) antagonist.

Anti-Obesity Agents

In one embodiment of the invention, the compounds of the formula I are administered in combination with a lipase inhibitor such as, for example, orlistat.

In one embodiment, the further active ingredient is fenfluramine or dexfenfluramine. In another embodiment, the further active ingredient is sibutramine.

In a further embodiment, the compounds of the formula I are administered in combination with CART modulators (see "*Cocaine-Amphetamine-Regulated Transcript Influences Energy Metabolism, Anxiety and Gastric Emptying in Mice*" Asakawa, A, et al., M.: Hormone and Metabolic Research (2001), 33(9), 554-558), NPY antagonists, e.g. naphthalene-1-sulfonic acid {4-[(4-aminoquinazolin-2-ylamino)methyl]-cyclohexyl-methyl}amide hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide; (WO 01/91752)), orexin antagonists (e.g. 1-(2-methylbenzoxazol-6-yl)-3-[1,5]naphthyridin-4-ylurea hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]-ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexyl-ethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tert-butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (Bromocriptine, Doprexin), lipase/amylase inhibitors (e.g. WO 00/40569), PPAR modulators (e.g. WO 00/78312), RXR modulators or TR-β agonists).

In one embodiment of the invention, the secondary active ingredient is leptin.

In one embodiment, the further active ingredient is dexamphetamine, amphetamine, mazindole or phentermine.

In one embodiment, the compounds of the formula I are as administered in combination with medicaments having effects on the coronary circulation and the vascular system, such as, for example, ACE inhibitors (e.g. ramipril), medicaments which act on the angiotensin-renin system, calcium antagonists, beta blockers etc.

In one embodiment, the compounds of the formula I are administered in combination with medicaments having an anti-inflammatory effect.

In one embodiment, the compounds of the formula are administered in combination with pharmaceutical agents which are employed for cancer therapy and cancer prevention.

It will be appreciated that every suitable combination of the compounds of the invention with one or more of the aforementioned compounds and optionally one or more other pharmacologically active substances is regarded as falling within the scope of the claims of the present invention. The examples detailed below are provided to better describe and more specifically set forth the compounds, processes and methods of the present invention. It is to be recognized that they are for illustrative purposes only however, and should not be interpreted as limiting the spirit and scope of the invention as later recited by the claims that follow.

EXAMPLES

1) Determination of EC50 Values of PPAR Agonists in the Cellular PPARalpha Assay The activity of the novel compounds of the present invention was tested as follows The potency of substances which bind to human PPARalpha and activate it in an agonistic manner is analyzed using a stably transfected HEK cell line (HEK=human embryo kidney) which is referred to here as PPARalpha reporter cell line. It contained two genetic elements, a luciferase reporter element (pdeltaM-GAL4-Luc-Zeo) and a PPARalpha fusion protein (GR-GAL4-humanPPARalpha-LBD) which mediates expression of the luciferase reporter element depending on a PPARalpha ligand. The stably and constitutively expressed fusion protein GR-GAL4-humanPPARalpha-LBD binds in the cell nucleus of the PPARalpha reporter cell line via the GAL4 protein portion to the GAL4 DNA binding motifs 5'-upstream of the luciferase reporter element which was stably integrated in the genome of the cell line. There is only little expression of the luciferase reporter gene without addition of a PPARalpha ligand if fatty acid-depleted fetal calf serum (cs-FCS) is used in the assay. PPARalpha ligands bind and activate the PPARalpha fusion protein and thereby bring about expression of the luciferase reporter gene. The luciferase which is formed can be detected by means of chemiluminescence via an appropriate substrate.

2) Construction of the Cell Line

The PPARalpha reporter cell line was prepared in two steps. Firstly, the luciferase reporter element was constructed and stably transfected into HEK cells. For this purpose, five binding sites of the yeast transcription factor GAL4 (in each case 5'-CGGAGTACTGTCCTCCGAG-3') were cloned in 5'-upstream of a 68 bp-long minimal MMTV promoter (Genbank Accession #V01175). The minimal MMTV promoter section contains a CCAAT box and a TATA element in order to enable efficient transcription by RNA polymerase II. The cloning and sequencing of the GAL4-MMTV construct took place in analogy to the description of Sambrook J. et. al. (Molecular Cloning, Cold Spring Harbor Laboratory Press, 1989). Which is hereby incorporated by reference herein.

The complete *Photinus pyralis* luciferase gene (Genbank Accession #M15077) was cloned in 3'-downstream of the GAL4-MMTV element. After sequencing, the luciferase reporter element consisting of five GAL4 binding sites, MMTV promoter and luciferase gene was subcloned into a plasmid which confers zeozin resistance in order to obtain the plasmid pdeltaM-GAL4-Luc-Zeo. This vector was transfected into HEK cells in accordance with the statements in Ausubel, F.M. et al. (Current Protocols in Molecular Biology, Vol. 1-3, John Wiley & Sons, Inc., 1995). Then zeozin-containing medium (0.5 mg/ml) was used to select a suitable stable cell clone which showed very low basal expression of the luciferase gene.

In a second step, the PPARalpha fusion protein (GR-GAL4-humanPPARalpha-LBD) was introduced into the stable cell clone described. For this purpose, initially the cDNA coding for the N-terminal 76 amino acids of the glucocorticoid receptor (Genbank Accession # P04150) was linked to the cDNA section coding for amino acids 1-147 of the yeast transcription factor GAL4 (Genbank Accession #P04386). The cDNA of the ligand-binding domain of the human PPARalpha receptor (amino acids S167-Y468; Genbank Accession #S74349) was cloned in at the 3' end of this GR-GAL4 construct. The fusion construct prepared in this way (GR-GAL4-humanPPARalpha-LBD) was subcloned into the plasmid pcDNA3 (from Invitrogen) in order to enable constitutive expression therein by the cytomegalovirus promoter. This plasmid was linearized with a restriction endonuclease and stably transfected into the previously described cell clone containing the luciferase reporter element. The finished PPARalpha reporter cell line which contains a luciferase reporter element and constitutively expresses the PPARalpha fusion protein (GR-GAL4-humanPPARalpha-LBD) was isolated by selection with zeozin (0.5 mg/ml) and G418 (0.5 mg/ml).

3) Assay Procedure

The activity of PPARalpha agonists was determined in a 3-day assay which is described below:

Day 1

The PPARalpha reporter cell line was cultivated to 80% confluence in DMEM medium (#41965-039, Invitrogen) which is mixed with the following additions: 10% cs-FCS (fetal calf serum; #SH-30068.03, Hyclone), 0.5 mg/ml zeozin (#R250-01, Invitrogen), 0.5 mg/ml G418 (#10131-027, Invitrogen), 1% penicillin-streptomycin solution (#15140-122, Invitrogen) and 2 mM L-glutamine (#25030-024, Invitrogen). The cultivation takes place in standard cell culture bottles (#353112, Becton Dickinson) in a cell culture incubator at 37° C. in the presence of 5% $CO_2$. The 80%-confluent cells are washed once with 15 ml of PBS (#14190-094, Invitrogen), treated with 3 ml of trypsin solution (#25300-054, Invitrogen) at 37° C. for 2 min, taken up in 5 ml of the DMEM medium described and counted in a cell counter. After dilution to 500 000 cells/ml, 35 000 cells are seeded in each well of a 96-well microtiter plate with a clear plastic base (#3610, Corning Costar). The plates are incubated in a cell culture incubator at 37° C. and 5% $CO_2$ for 24 h.

Day 2

PPARalpha agonists to be tested are dissolved in DMSO in a concentration of 10 mM. This stock solution is diluted in DMEM medium (#41965-039, Invitrogen) which is mixed with 5% cs-FCS (#SH-30068.03, Hyclone), 2 mM L-glutamine (#25030-024, Invitrogen) and the previously described antibiotics (zeozin, G418, penicillin and streptomycin).

Test substances are tested in 11 different concentrations in the range from 10 µM to 100 pM. More potent compounds are tested in concentration ranges from 1 µM to 10 pM or between 100 nM and 1 pM.

The medium of the PPARalpha reporter cell line seeded on day 1 is completely removed by aspiration, and the test substances diluted in medium are immediately added to the cells. The dilution and addition of the substances is carried out by a robot (Beckman FX). The final volume of the test substances diluted in medium is 100 µl per well of a 96-well microtiter plate. The DMSO concentration in the assay is less than 0.1% v/v in order to avoid cytotoxic effects of the solvent.

Each plate was charged with a standard PPARalpha agonist, which was likewise diluted in 11 different concentrations, in order to demonstrate the functioning of the assay in each individual plate. The assay plates are incubated in an incubator at 37° C. and 5% $CO_2$ for 24 h.

Day 3

The PPARalpha reporter cells treated with the test substances are removed from the incubator, and the medium is aspirated off. The cells are lyzed by pipetting 50 µl of Bright Glo reagent (from Promega) into each well of a 96-well microtiter plate. After incubation at room temperature in the dark for 10 minutes, the microtiter plates are measured in the luminometer (Trilux from Wallac). The measuring time for each well of a microtiter plate is 1 sec.

The raw data from the luminometer are transferred into a Microsoft Excel file. Dose-effect plots and EC50 values of PPAR agonists are calculated using the XL.Fit program as specified by the manufacturer (IDBS).

4) Determination of EC50 Values of PPAR Agonists in the Cellular PPARgamma Assay A transient transfection system is employed to determine the cellular PPARgamma activity of PPAR agonists. It is based on the use of a luciferase reporter plasmid (pGL3basic-5xGAL4-TK) and of a PPARgamma expression plasmid (pcDNA3-GAL4-humanPPARgammaLBD). Both plasmids are transiently transfected into human embryonic kidney cells (HEK cells). There is then expression in these cells of the fusion protein GAL4-humanPPARgammaLBD which binds to the GAL4 binding sites of the reporter plasmid. In the presence of a PPARgamma-active ligand, the activated fusion protein GAL4-humanPPARgammaLBD induces expression of the luciferase reporter gene, which can be detected in the form of a chemiluminescence signal after addition of a luciferase substrate. As a difference from the stably transfected PPARalpha reporter cell line, in the cellular PPARgamma assay the two components (luciferase reporter plasmid and PPARgamma expression plasmid) are transiently transfected into HEK cells because stable and permanent expression of the PPARgamma fusion protein is cytotoxic.

5) Construction of the Plasmids

The luciferase reporter plasmid pGL3basic-5xGAL4-TK is based on the vector pGL3basic from Promega. The reporter plasmid is prepared by cloning five binding sites of the yeast transcription factor GAL4 (each binding site with the sequence 5'-CTCGGAGGACAGTACTCCG-3'), together with a 160 bp-long thymidine kinase promoter section (Genbank Accession #AF027128) 5'-upstream into pGL3basic. 3'-downstream of the thymidine kinase promoter is the complete luciferase gene from Photinus pyralis (Genbank Accession # Ml 5077), which is already a constituent of the plasmid pGL3basic used. The cloning and sequencing of the reporter plasmid pGL3basic-5xGAL4-TK took place in analogy to the description in Sambrook J. et. al. (Molecular cloning, Cold Spring Harbor Laboratory Press, 1989).

The PPARgamma expression plasmid pcDNA3-GAL4-humanPPARgammaLBD was prepared by first cloning the cDNA coding for amino acids 1-147 of the yeast transcription factor GAL4 (Genbank Accession #P04386) into the plasmid pcDNA3 (from Invitrogen) 3'-downstream of the cytomegalovirus promoter. Subsequently, the cDNA of the ligand-binding domain (LBD) of the human PPARgamma receptor (amino acids 1152-Y475; Accession #g1480099) 3'-downstream of the GAL4 DNA binding domain was cloned. Cloning and sequencing of the PPARgamma expression plasmid pcDNA3-GAL4-humanPPARgammaLBD again took place in analogy to the description in Sambrook J. et. al. (Molecular cloning, Cold Spring Harbor Laboratory Press, 1989). Besides the luciferase reporter plasmid pGL3basic-5xGAL4-TK and the PPARgamma expression plasmid pcDNA3-GAL4-humanPPARgammaLBD, also used for the cellular PPARgamma assay are the reference plasmid pRL-CMV (from Promega) and the plasmid pBluescript SK(+) from Stratagene. All four plasmids were prepared using a plasmid preparation kit from Qiagen, which ensured a plasmid quality with a minimal endotoxin content, before transfection into HEK cells.

6) Assay Procedure

The activity of PPARgamma agonists is determined in a 4-day assay which is described below. Before the transfection, HEK cells were cultivated in DMEM medium (#41965-039, Invitrogen) which was mixed with the following additions: 10% FCS (#16000-044, Invitrogen),1% penicillin-streptomycin solution (#15140-122, Invitrogen) and 2 mM L-glutamine (#25030-024, Invitrogen).

Day 1

Solution A, a transfection mixture which contains all four plasmids previously described in addition to DMEM medium, was prepared. The following amounts are used to make up 3 ml of solution A for each 96-well microtiter plate for an assay: 2622 µl of antibiotic- and serum-free DMEM medium (#41965-039, Invitrogen), 100 µl of reference plasmid pRL-CMV (1 ng/µl), 100 µl of luciferase reporter plasmid pGL3basic-5xGAL4-TK (10 ng/µl), 100 µl of PPARgamma expression plasmid pcDNA3-GAL4-humanPPARgammaLBD (100 ng/µl) and 78 µl, of plasmid pBluescript SK(+) (500 ng/µl). Then 2 ml of solution B are prepared by mixing 1.9 ml of DMEM medium (#41965-039, Invitrogen) with 100 µl of PolyFect transfection reagent (from Qiagen) for each 96-well microtiter plate. Subsequently, 3 ml of solution A are mixed with 2 ml of solution B to give 5 ml of solution C, which is thoroughly mixed by multiple pipetting and incubated at room temperature for 10 min.

80%-confluent HEK cells from a cell culture bottle with a capacity of 175 cm$^2$ are washed once with 15 ml of PBS (#14190-094, Invitrogen) and treated with 3 ml of trypsin solution (#25300-054, Invitrogen) at 37° C. for 2 min. The cells are then taken up in 15 ml of DMEM medium (#41965-039, Invitrogen) which is mixed with 10% FCS (#16000-044, Invitrogen),1% penicillin-streptomycin solution (#15140-122, Invitrogen) and 2 mM L-glutamine (#25030-024, Invitrogen). After the cell suspension has been counted in a cell counter, the suspension is diluted to 250 000 cells/ml.

15 ml of this cell suspension are mixed with 5 ml of solution C for one microtiter plate. 200 µl of the suspension are seeded in each well of a 96-well microtiter plate with a clear plastic base (#3610, Corning Costar). The plates are incubated in a cell culture incubator at 37° C. and 5% $CO_2$ for 24 h.

Day 2

PPAR agonists to be tested are dissolved in DMSO in a concentration of 10 mM. This stock solution is diluted in DMEM medium (#41965-039, Invitrogen) which is mixed with 2% Ultroser (#12039-012, Biosepra), 1% penicillin-streptomycin solution (#15140-122, Invitrogen) and 2 mM L-glutamine (#25030-024, Invitrogen). Test substances are tested in a total of 11 different concentrations in the range from 10 µM to 100 pM. More potent compounds are tested in concentration ranges from 1 µM to 10 pM.

The medium of the HEK cells transfected and seeded on day 1 is completely removed by aspiration, and the test substances diluted in medium are immediately added to the cells. The dilution and addition of the substances is carried out by a robot (Beckman FX). The final volume of the test substances diluted in medium is 100 µl per well of a 96-well microtiter plate. Each plate is charged with a standard PPARgamma agonist, which is likewise diluted in 11 different concentrations, in order to demonstrate the functioning of the assay in each individual plate. The assay plates are incubated in an incubator at 37° C. and 5% $CO_2$ for 48 h.

Day 4

After removal of the medium by aspiration, 50 µl of Dual-Glo™ reagent (Dual-Glo™ Luciferase Assay System; Promega) are added to each well in accordance with the manufacturer's instructions in order to lyze the cells and provide the substrate for the firefly luciferase (Photinus pyralis) formed in the cells. After incubation at room temperature in the dark for 10 minutes, the firefly luciferase-mediated chemiluminescence is measured in a measuring instrument (measuring time/well 1 sec; Trilux from Wallac). Then 50 µl of the Dual-Glo™ Stop & Glo reagent (Dual-Glo™ Luciferase Assay System; Promega) is added to each well in order to stop the activity of the firefly luciferase and provide the substrate for the Renilla luciferase expressed by the reference plasmid pRL-CMV. After incubation at room temperature in the dark for a further 10 minutes, the chemiluminescence mediated by the Renilla luciferase is again measured for 1 sec/well in the measuring instrument.

The raw data from the luminometer are transferred into a Microsoft Excel file. The firefly/Renilla luciferase activity ratio is determined for each measurement derived from one well of the microtiter plate. The dose-effect plots and EC50 values of PPAR agonists are calculated from the ratios by the XL.Fit program as specified by the manufacturer (IDBS).

The results for the activity of some compounds of the invention of the formula I are indicated in Table I below:

TABLE I

| Example No | Formula | EC50 PPARalpha [µM] | EC50 PPARgamma [µM] |
|---|---|---|---|
| 1 | | 0.0036 | 1.5601 |
| 2 | | 0.0320 | 0.2322 |
| 3 | | 0.1522 | 2.7564 |
| 4 | | 0.0019 | 0.3235 |
| 5 | | 0.0143 | 0.2656 |
| 6 | | 0.0193 | 1.8831 |
| 7 | | 0.0462 | 0.7996 |

TABLE I-continued

| Example No | Formula | EC50 PPARalpha [μM] | EC50 PPARgamma [μM] |
|---|---|---|---|
| 8 | | 0.0375 | 1.5008 |
| 9 | | 0.0488 | 0.4917 |
| 10 | | 0.3813 | 0.6722 |
| 11 | | 0.0709 | 1.7876 |
| 12 | | 0.0055 | 0.1333 |
| 13 | | 0.3133 | 0.1242 |
| 14 | | 0.0187 | 0.1270 |
| 15 | | 0.0717 | 0.1495 |
| 16 | | 0.0127 | 0.1992 |
| 17 | | 0.0420 | 0.1090 |
| 18 | | 0.0205 | 0.0383 |
| 19 | | 0.0018 | 0.1924 |
| 20 | | 0.1495 | 0.0714 |
| 21 | | 0.0016 | 0.1843 |
| * | cis/racemate | 0.075 | 2.592 |
| ** | cis/racemate | 0.0013 | >10 |

\* Example 58 from WO 2004/076427.
\*\* Example 61 from WO 2004/076427.

It is evident from Table I that the compounds of the invention of the formula I activate he PPARalpha receptor and the PPARgamma receptor and thus for example bring about a lowering of triglycerides in the body in analogy to fibrates in clinical use (see, or example, J.-Ch. Fruchard et al.,: PPARS, Metabolic Disease and Atherosclerosis, Pharmacological Research, Vol. 44, No. 5, 2001; S. Kersten et al.: *Roles of PPARs in Health and Disease,* NATURE, VOL 405, 25 MAY 2000; I. Pineda et al.: *Peroxisome Proliferator-Activated Receptors: from Transcriptional Control to Clinical Practice,* Curr Opin Lipidol 12: 2001, 245-254).all of which are hereby incorporated by reference herein.

TABLE IIa

| Ex. | R | R1 | R2 | R3 | R4 | R5 |
|---|---|---|---|---|---|---|
| 1 | H | CF3 | H | C2H5 | CH3 | H |
| 2 | H | H | CF3 | C2H5 | CH3 | H |
| 3 | CF3 | H | H | C2H5 | CH3 | H |
| 4 | H | CH3 | CH3 | C2H5 | CH3 | H |
| 5 | H | tert-C4H9 | H | C2H5 | CH3 | H |
| 6 | H | CF3 | H | i-C3H7 | CH3 | H |
| 7 | H | H | CF3 | i-C3H7 | CH3 | H |
| 8 | H | CH3 | CH3 | i-C3H7 | CH3 | H |
| 9 | H | tert-C4H9 | H | i-C3H7 | CH3 | H |
| 10 | H | H | OCH3 | i-C3H7 | CH3 | H |
| 11 | H | 2-Napthyl |  | i-C3H7 | CH3 | H |

TABLE IIb

| Ex. | R | R1 | R2 | R3 | R4 | R5 |
|---|---|---|---|---|---|---|
| 12 | H | CH3 | CH3 | i-C3H7 | CH3 | H |
| 13 | H | Ph | H | CH3 | CH3 | H |
| 14 | H | 2-Napthyl |  | i-C3H7 | CH3 | H |
| 15 | H | H | OCH3 | C2H5 | CH3 | H |
| 16 | H | H | CF3 | i-C3H7 | CH3 | H |
| 17 | H | i-C4H9 | H | i-C3H7 | CH3 | H |
| 18 | H | tert-C4H9 | H | i-C3H7 | CH3 | H |
| 19 | H | 2-Napthyl |  | C2H5 | CH3 | H |
| 20 | H | OPh | H | CH3 | CH3 | H |
| 21 | H | CH3 | CH3 | C2H5 | CH3 | H |

7) Processes

The compounds of formula I of the present invention may be chemically synthesized in accordance with the following reaction schemes:

Process A:

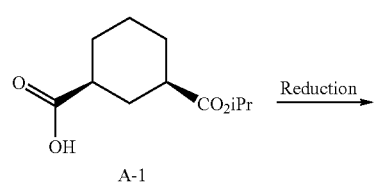

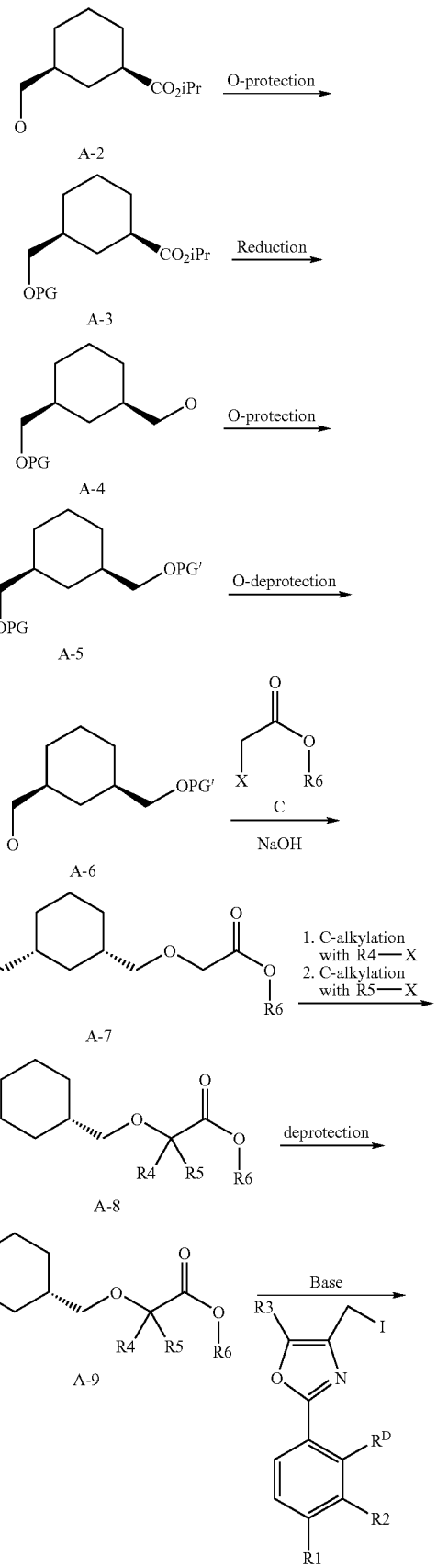

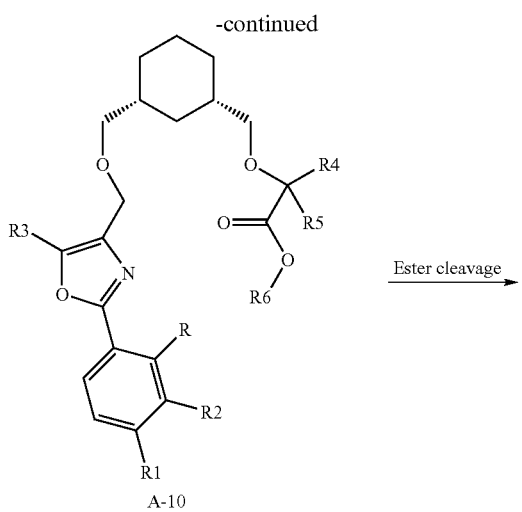

A-10

Ester cleavage →

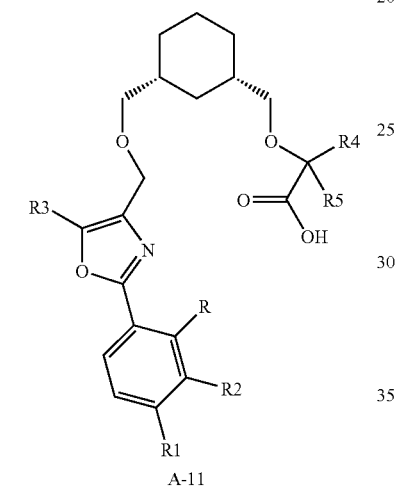

A-11

Compound A-1 (prepared as described by N. W. Boaz, Tetrahedron: Asymmetry, (1999) 10, 813-816) is reduced to the alcohol A-2 (e.g. with ethyl chloroformate, triethylamine and sodium borohydride in THF or with isobutyl chloroformate and N-methylmorpholine and sodium borohydride in THF) and subsequently protected on the primary hydroxyl group with a protective group PG (for example for PG=THP; by stirring with dihydropyran and toluenesulfonic acid monohydrate in dichloromethane at RT), resulting in the compound A-3. A-3 is reduced with lithium aluminum hydride in an etheral solvent to the compound A-4. The compound A-4 is protected on the primary hydroxyl group with a protective group PG' which is orthogonal to PG (for example for PG=TBDPS: by stirring with TBDPSCl and imidazole in DMF at RT), resulting in the compound A-5. The compound A-5 is deprotected on one side (for example for DG=THP: by stirring with toluenesulfonic acid monohydrate or pyridinium p-toluenesulfonate in methanol or isopropanol at RT), resulting in the compound A-6.

The compound A-6 is reacted with compound C—an ester of 2-haloacetic acid (halogen can be bromine or chlorine) and of the alcohol R6-OH in which R6 has the meaning described above—to give the compound A-7. The compound A-7 is reacted with a lithium amide base (e.g. lithium diisopropylamide or lithium-2,2,5,5-tetramethylpyrrolidide) and an alkyl halide of the general formula R4X, in which R4 has the meaning described above, in an etheral solvent at low temperature. The compound obtained in this way is then reacted with a lithium amide base (e.g. lithium diisopropylamide or lithium-2,2,5,5-tetramethylpyrrolidide) and an alkyl halide of the general formula R5X, in which R5 has the meaning described above, in an etheral solvent at low temperature to give the compound A-8. The protective group SG' is eliminated from A-8 (in the case of PG=TBDPS with tetrabutylammonium fluoride in THF), resulting in the compound of the general formula A-9. The compound A-9 is reacted with a base (for example sodium hydride or potassium tert-butoxide) and the compound D in which R1, R2 and R3 have the meanings described above in an etheral solvent to give the compound A-10. The compound A-10 is hydrolyzed to the acid A-11: in the case where R6 are primary or secondary alkyl radicals, with a base in methanol, or in the case where R6 is a tertiary alkyl radical, with anhydrous acid in an inert solvent (for example hydrogen chloride in dioxane or trifluoroacetic acid in dichloromethane).

Examples 1 to 11 were synthesized according to the following process.

Process B:

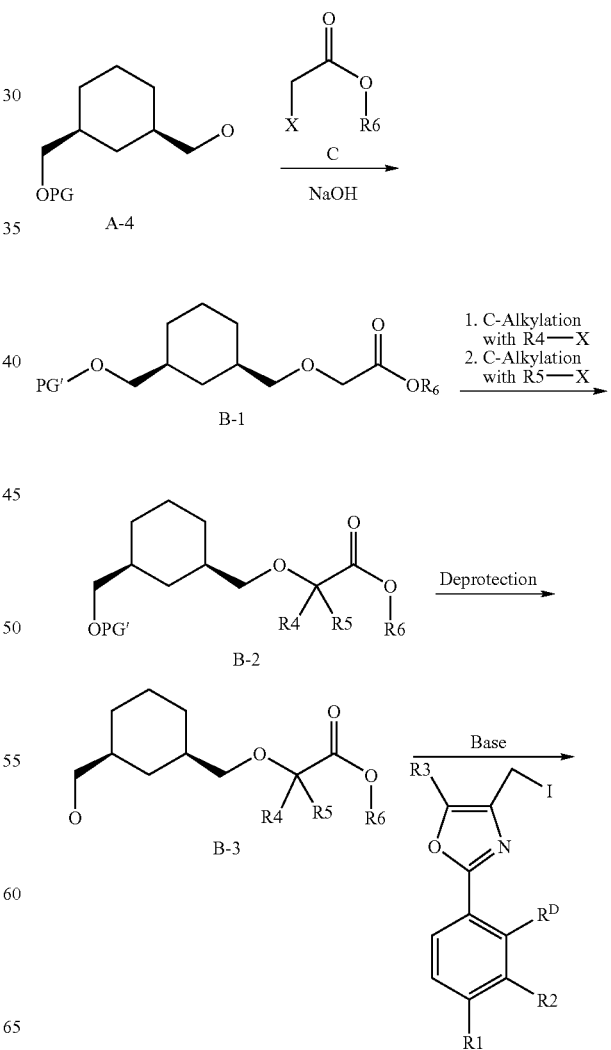

-continued

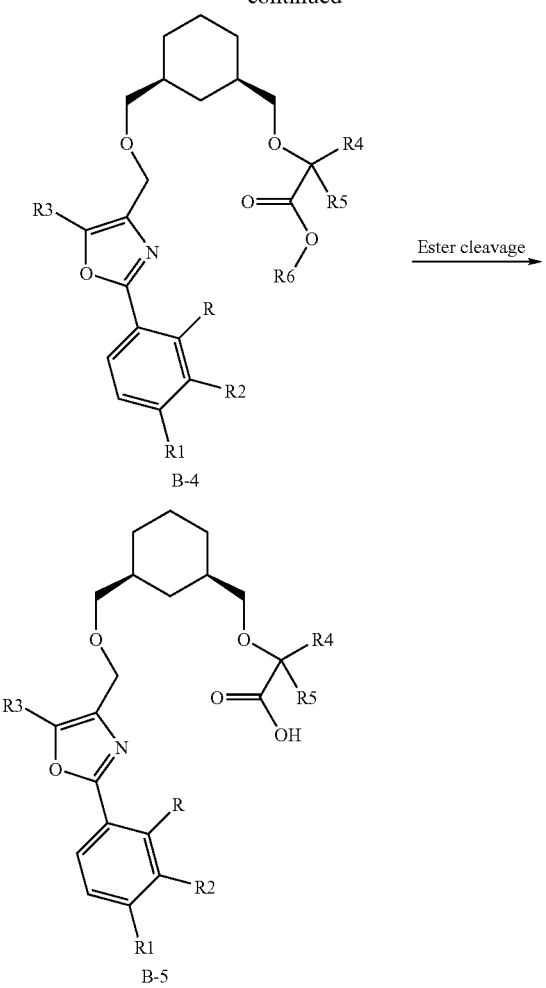

The compound A-4 (see process A) was reacted with compound C—an ester of 2-haloacetic acid (halogen can be bromine or chlorine) and of the alcohol R6-OH in which R6 has the meaning described above—to give the compound B-1. The compound B-1 is reacted with a lithium amide base (e.g. lithium diisopropylamide) and an alkyl halide of the general formula R4X in which R4 has the meaning described above in an etheral solvent at low temperature. The compound obtained in this way is then reacted with a lithium amide base (e.g. lithium diisopropylamide) and an alkyl halide of the general formula R5X in which R5 has the meaning described above in an etheral solvent at low temperature to give the compound B-3. The protective group PG is eliminated from B-2, resulting in the compound of the general formula B-3. The compound B-3 is reacted with a base (for example sodium hydride or potassium tert-butoxide) and the compound D in which R1, R2 and R3 have the meanings described above in an etheral solvent to give the compound B-4. The compound B-4 is hydrolyzed to the acid B-5: in the case where R6 are primary or secondary alkyl radicals, with a base in methanol, or in the case where R6 is a tertiary alkyl radical, with anhydrous acid in an inert solvent (for example hydrogen chloride in dioxane or trifluoroacetic acid in dichloromethane).

The enantiomeric products of Examples 12-21 can be synthesized by this process.

The abbreviations used stand for:
Ac Acetyl
Bn Benzyl
Bu Butyl
iBu Isobutyl
tBu tert-Butyl
BuLi n-Butyllithium
Bz Benzoyl
Cy Cyclohexyl
DCI Direct chemical ionization (in MS)
DCM Dichloromethane
DHP 2,3-Dihydropyran
DMAP 4-N,N-Dimethylaminopyridine
DMF N,N-Dimethylformamide
DMSO Dimethyl sulfoxide
EA Ethyl acetate
EDC N'-(3-Dimethylaminopropyl)-N-ethylcarbodiimide× HCl
EI Electron impact ionization (in MS)
equiv. Equivalent
ESI Electron spray ionization (in MS)
Et Ethyl
h Hour
HATU O-(7-Azabenzotriazol-1-yl)-N,N,N',N'-tetramethyluronium hexafluorophosphate
HOBt 1-Hydroxy-1H-benzotriazole×H2O
HPLC High pressure, high performance liquid chromatography
LC-MS Coupled liquid chromatography—mass spectroscopy
Me Methyl
MS Mass spectroscopy
MsCl Methanesulfonyl chloride
MTBE tert-Butyl methyl ether
NMR Nuclear magnetic resonance spectroscopy
Pd/C Palladium on carbon
Ph Phenyl
iPr Isopropyl
nPr n-Propyl
Rf Retention ratio (in TLC)
RT Room temperature
sat. Saturated
TBAF Tetrabutylammonium fluoride
TBAI Tetrabutylammonium iodide
TBDPSCI tert-Butyldiphenylsilyl chloride
TBDMSCI tert-Butyldimethylsilyl chloride
TFA Trifluoroacetic acid
THF Tetrahydrofuran
THP Tetrahydropyranyl
TLC Thin layer chromatography
Tr Trityl
TsOH Toluene sulfonic acid Other compounds can be prepared in accordance with the abovementioned processes.

Building block synthesis of the compounds of the general formula A-8:

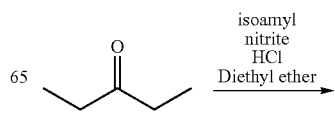

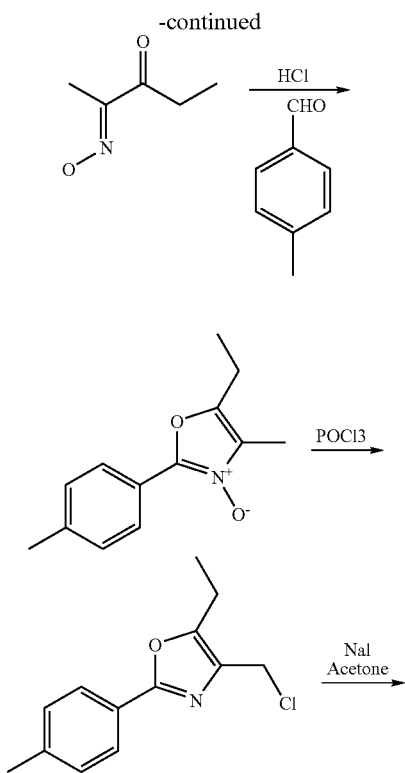
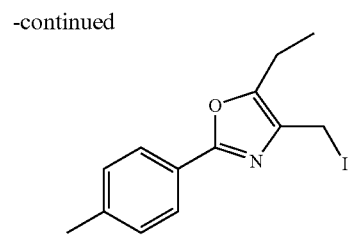

Diethyl ketone is reacted with isoamyl nitrite and HCl in diethyl ether, resulting in pentane-2,3-dione 2-oxime (G. Buechi, J. Galindo, J. Org. Chem. (1991) 56(8), 2605-2606). The latter is reacted with p-methylbenzaldehyde and HCl in acetic acid to give 5-ethyl-4-methyl-2-p-tolyloxazole 3-oxide (P. M. Weintraub, J. Med. Chem. (1972) 15(4), 419-420). Boiling this compound with phosphoryl chloride in chloroform results in 4-chloromethyl-5-ethyl-2-p-tolyloxazole (M. S. Malamas, R. P. Carlson, D. Grimes, R. Howell, K. Glaser, I. Gunawan, J. A. Nelson, M. Kanzelberger, U. Shah, D. A. Hartman, J. Med. Chem. (1996) 39(1), 237-245). This compound is heated with sodium iodide in acetone under reflux, resulting in 5-ethyl-4-iodomethyl-2-p-olyloxazole (A., Ziatkov, P., Peikov, J., Rodriguez-Alvarez, N., Danchev, I., Nikolova, J., Mitkov, Eur. J. Med. Chem. Chim. Ther. (2000) 35(10), 941-948). These are also incorporated herein by reference The following intermediate building blocks in the reaction schemes are obtained in analogy to the synthesis from the precursors depicted in Table III:

TABLE III

| No. | Ketone | Aldehyde | Product |
|---|---|---|---|
| 1 | | | |
| 2 | | | |
| 3 | | | |
| 4 | | | |
| 5 | | | |

TABLE III-continued

| No. | Ketone | Aldehyde | Product |
|---|---|---|---|
| 6 | | | |
| 7 | | | |
| 8 | | | |
| 9 | | | |
| 10 | | | |
| 11 | | | |
| 12 | | | |
| 13 | | | |

TABLE III-continued
| No. | Ketone | Aldehyde | Product |
|-----|--------|----------|---------|
| 14 | | | |
| 15 | | | |
| 16 | | | |
| 17 | | | |
Example 1
A) Preparation of 2-{(1S, 3R)-3-[5-Ethyl-2-(4-trifluoromethylphenyl)-oxazol-4-ylmethoxymethyl]cyclohexylmethoxy}-2-methylpropionic acid
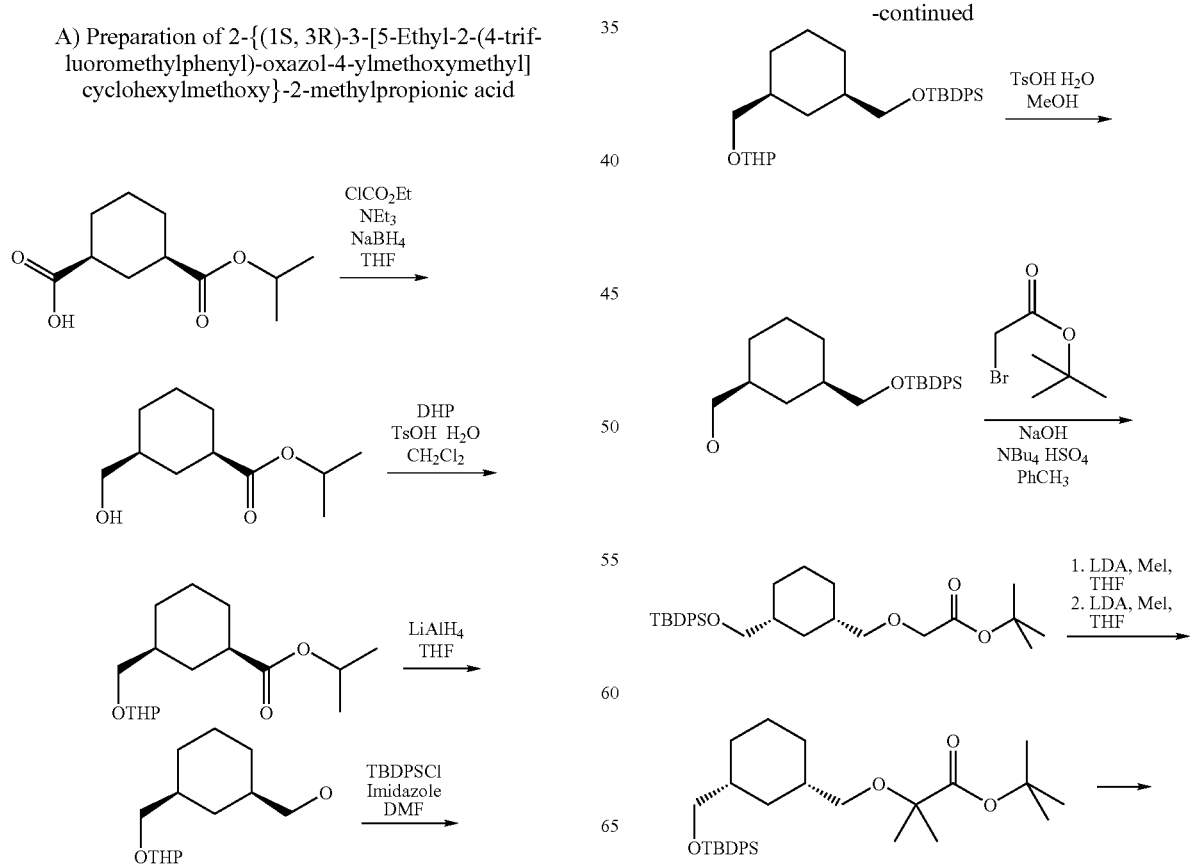

-continued

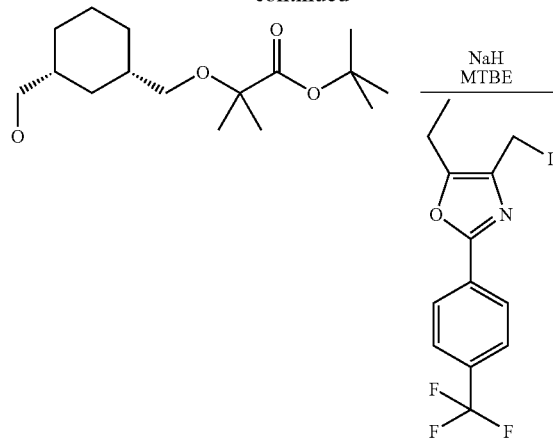

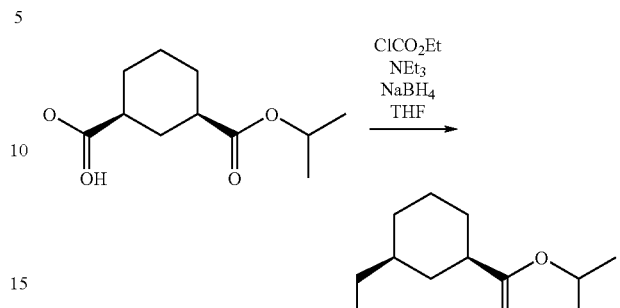

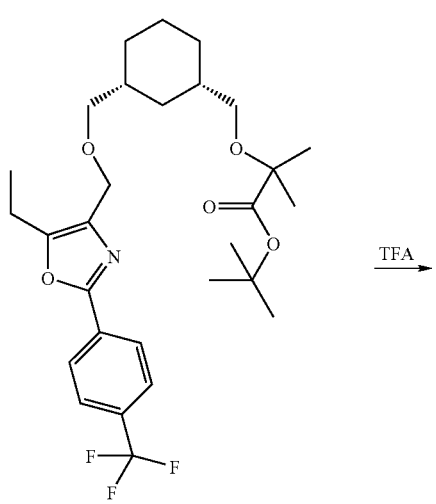

b) Preparation of Isopropyl (1R,3S)-3-hydroxymethylcyclohexanecarboxylate

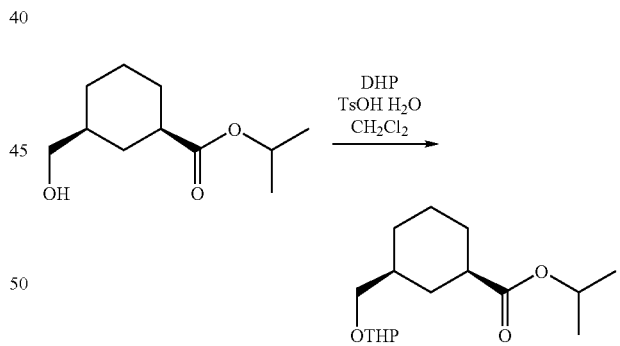

140 g of (1S,3R)-3-isopropoxycarbonylcyclohexanecarboxylic acid are dissolved in THF, and 100 ml of triethylamine was added. At −10° C., 68.4 ml of ethyl chloroformate were added dropwise, and the suspension was stirred overnight. After filtration through celite, 55 g of sodium borohydride are added at 0° C., and the suspension is stirred at RT for a further 6 h. A further 25 g of sodium borohydride are added, and the suspension is stirred overnight. Water is added and the solution was stirred for 2 h. The phases are separated and the aqueous phase is extracted with MTBE, and the combined organic phases were washed with sat. NaCl solution, dried over MgSO4 and concentrated. 105 g of isopropyl (1R,3S)-3-hydroxymethylcyclohexanecarboxylate were obtained as a colorless oil.

$C_{11}H_{20}O_3$ (200.28): LCMS (ESI): 201.2 [MH$^+$].

c) Preparation of Isopropyl (1R,3S)-3-(tetrahydropyran-2-yloxymethyl)cyclohexanecarboxylate

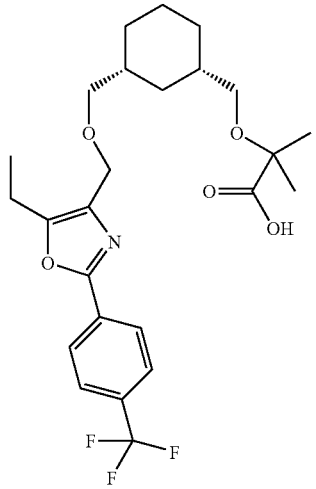

100 g of isopropyl (1R,3S)-3-hydroxymethylcyclohexanecarboxylate and 46.2 g of dihydropyran are dissolved in 500 ml of dichloromethane and, at 0° C., 4.75 g of toluenesulfonic acid monohydrate are added. The solution is stirred overnight and then sat. sodium bicarbonate solution is added. The organic phase is separated off, diluted with MTBE and washed with sat. sodium chloride solution, dried over MgSO4 and concentrated, resulting in 140 g of isopropyl (1R,3S)-3-(tetrahydropyran-2-yloxymethyl)cyclohexanecarboxylate as brown oil.

$C_{16}H_{28}O_4$ (284.4); MS (Cl+): 285 (5) [MH$^+$], 201 (100) [MH$^+$—C5H8O], 85 (77).

d) Preparation of (1R,3S)-3-(Tetrahydropyran-2-yloxymethyl)cyclohexylmethanol

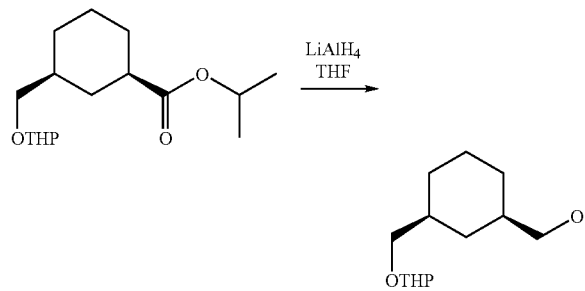

60.6 g of isopropyl (1R,3S)-3-(tetrahydropyran-2-yloxymethyl)cyclohexanecarboxylate were dissolved in 100 ml of THF and, at 0° C., were added dropwise to a suspension of 16.2 g of lithium aluminum hydride in 300 ml of THF. The mixture is stirred at RT until precursor is no longer detectable by TLC. 50 ml of 10N KOH are added to the mixture at 0° C. The solution above the gray precipitate is decanted off, and the residue is digested with ethyl acetate and filtered. The combined filtrates are evaporated, the residue is extracted with ethyl acetate, and the org. phases are dried over MgSO4 and concentrated. The residue is chromatographed on silica gel (heptane/ethyl acetate gradient), resulting in 30.7 g of (1R,3S)-3-(tetrahydropyran-2-yloxymethyl)cyclo-hexyl-methanol as yellow oil.

$C_{13}H_{24}O_3$ (228.17); MS (Cl+): 229.4 (24) [MH$^+$], 145.4 (9) [MH$^+$—C5H8O], 85.2 (100).

e) Preparation of (1S,3R)-3-(tert-Butyldiphenylsilanyloxymethyl)-cyclohexylmethanol

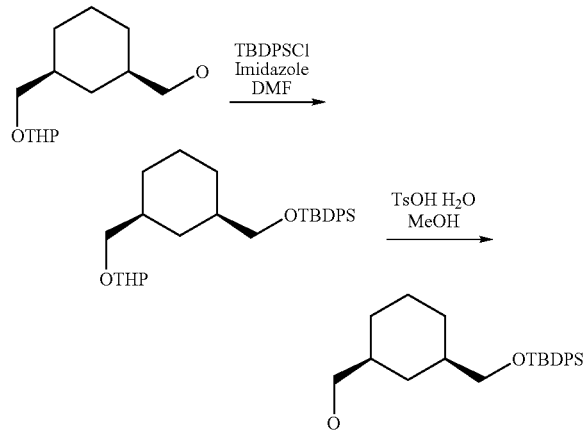

36.2 g of (1R,3S)-3-(tetrahydropyran-2-yloxymethyl)cyclohexylmethanol are dissolved in 190 ml of DMF and 130 ml of toluene, and 27.0 g of imidazole are added. At 0° C., 47.9 g of tert-butyldiphenylchlorosilane are added dropwise, and the solution is stirred at RT overnight. The solution is concentrated, the residue is taken up in MTBE and water, the aqueous phase is extracted once more with MTBE, and the combined org. phases are washed twice with water and once with saturated sodium chloride solution, dried over MgSO4 and concentrated. This results in tert-butyldiphenyl-[(1R,3S)-3-(tetrahydropyran-2-yloxymethyl)cyclohexylmethoxy] silane as yellow oil in quantitative yield.

The latter is dissolved in 400 ml of isopropanol and, after addition of 1.52 g of p-toluenesulfonic acid, stirred at RT for 48. Subsequently, sat. NaHCO3 solution is added until a neutral reaction is observed with pH paper. The solvent is substantially distilled off. The aqueous residue is taken up in water and MTBE. The aqueous phase is separated off and extracted three times with MTBE. The combined org. phases are washed with water and sat. NaCl solution, dried over MgSO4 and concentrated, resulting in 67 g of (1S,3R)-3-(tert-butyldiphenylsilanyloxymethyl)cyclohexylmethanol as yellow oil.

$C_{24}H_{34}O_2Si$ (382.62): LCMS (ESI): 383.5 [MH$^+$].

f) Preparation (1S,3R)-3-(tert-butyldiphenylsilanyloxymethyl)cyclohexylmethoxyl-2-methylpropionate

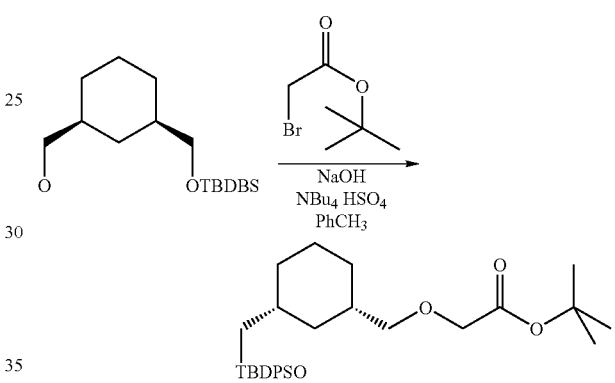

67 g of (1S,3R)-3-(tert-butyldiphenylsilanyloxymethyl) cyclohexylmethanol, 86.3 g of tert-butyl bromoacetate, 19.8 g of tetrabutylammonium bisulfate are dissolved in 300 ml of toluene and, at 10° C. (ice-water bath), a solution of 70.8 g of sodium hydroxide in 73 ml of water is added, and the mixture is stirred vigorously (KPG paddle stirrer) at 1020 C. for 18 h. Then MTBE and water are added, and the phases are separated. The aqueous phase is extracted twice with MTBE, and the combined organic phases are washed with saturated sodium chloride solution, dried over magnesium sulfate and concentrated. The residue is chromatographed on silica gel (heptane/ethyl acetate gradient). This results in 60.7 g of tert-butyl 2-[(1S,3R)-3-(tert-butyldiphenylsilanyloxymethyl)cyclohexylmethoxy]-2-methylpropionate as pale yellow oil.

$C_{30}H_{44}O_4Si$ (496.30): LCMS (ESI): 514.49 [M$^+$+NH4]

g) Preparation of tert-Butyl 2-[(1S,3R)-3-(tert-butyl-diphenylsilanyloxymethyl)cyclohexylmethoxy]-2-methylpropionate

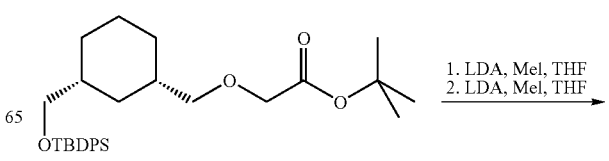

-continued

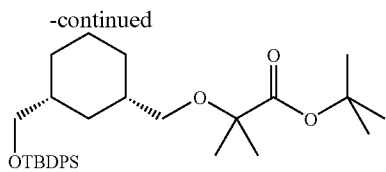

155 ml of a solution of lithium diisopropylamide (2M in THF) are added to a solution of 60.7 g of tert-butyl 2-[(1S,3R)-3-(tert-butyldiphenylsilanyloxymethyl)cyclohexylmethoxy]-2-methylpropionate in 180 ml of THF at −78° C., during which the temperature should not rise above −55° C. The solution is stirred at this temperature for 10 min and then warmed to 0° C. and stirred at this temperature for a further 15 min, after which the solution is cooled again to −78° C., and 38 ml of methyl iodide are added dropwise. The solution is warmed to 0° C. and then saturated NH4Cl solution and ethyl acetate are added. The phases are separated, the organic phase is washed with saturated NH4Cl solution, the combined aqueous phases are extracted once again with ethyl acetate, and then the combined organic phases are washed with saturated sodium chloride solution, dried over magnesium sulfate and concentrated. 150 ml of a solution of lithium diisopropylamide (2M in THF) are added to a solution of the residue obtained in this way in 180 ml of THF at −78° C., during which the temperature should not rise above −55° C. The solution is stirred at this temperature for 10 min and then warmed to −10° C. and stirred at this temperature for a further 15 min, after which the solution is cooled again to −78° C., and 38 ml of methyl iodide are added dropwise. The solution is warmed to −10° C. and then saturated NH4Cl solution and ethyl acetate are added. The phases are separated, the organic phase is washed with saturated NH4Cl solution, the combined aqueous phases are extracted once again with ethyl acetate, and then the combined organic phases are washed with saturated sodium chloride solution, dried over magnesium sulfate and concentrated. The residue is chromatographed on silica gel (heptane/ethyl acetate gradient) resulting in 51.2 g of tert-butyl 2-[(1S,3R)-3-(tert-butyldiphenylsilanyloxymethyl)cyclohexylmethoxy]-2-methylpropionate as brown oil.

1H-NMR (500 MHz, DMSO): ═=7.57-7.63 (m, 4H); 7.40-7.50 (m, 6H); 3.43-3.49 (m, 2H); 3.11-3.16 (m, 1H); 3.04-3.09 (m, 1H); 1.80-1.86 (m, 1H); 1.65-1.78 (m, 2H); 1.46-1.62 (m, 2H); 1.40 (s, 9H); 1.26 (s, 6H); 0.74-1.60 (m, 4H); 1.00 (s, 9H); 0.58-0.67 (m, 1H).

h) Preparation of tert-Butyl 2-((1R,3S)-3-hydroxymethylcyclohexylmethoxy)-2-methylpropionate

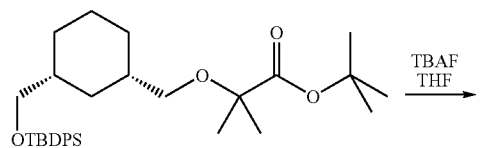

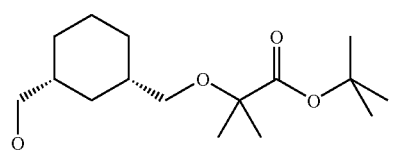

51.2 g of tert-butyl 2-[(1S,3R)-3-(tert-butyldiphenylsilanyloxymethyl)cyclo-hexylmethoxy]-2-methylpropionate are dissolved in 350 ml of THF and, after addition of 54.5 g of tetrabutylammonium fluoride hydrate, stirred at RT overnight. Most of the THF is distilled off, and the residue is taken up in MTBE/water. The organic phase is separated off, dried over MgSO4 and concentrated. The residue is chromatographed on silica gel (heptane/ethyl acetate gradient), resulting in 14.4 g of tert-butyl 2-((1R,3S)-3-hydroxymethylcyclohexylmethoxy)-2-methylpropionate as yellow oil.

1H-NMR (500 MHz, DMSO): ☐=4.30-4.36 (m, 1 H); 3.23-3.29 (m, 1H); 3.15-3.21 (m, 2H); 3.05-3.13 (m, 1H); 1.53-1.81 (m, 4H); 1.15-1.52 (m, 3H); 1.41 (s, 9H); 1.27 (s, 6H); 0.70-0.86 (m, 2H); 0.49-0.58 (m, 1H).

i) Preparation of tert-Butyl 2-{(1S,3R)-3-[5-ethyl-2-(4-trifluoromethylphenyl)oxazol-4-ylmethoxymethyl]cyclohexylmethoxy}-2-methylpropionate

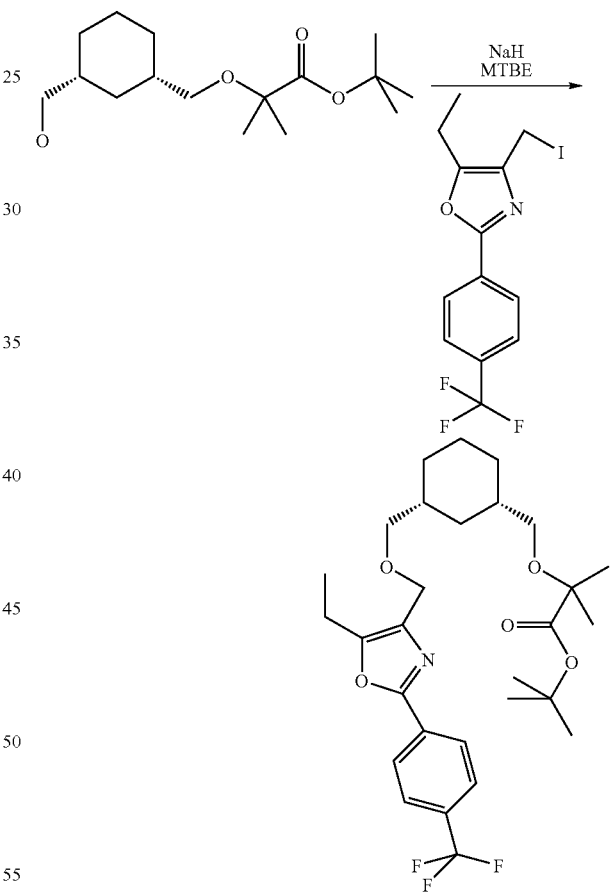

300 mg of tert-butyl 2-((1R,3S)-3-hydroxymethylcyclohexylmethoxy)-2-methylpropionate are dissolved in 10 ml of MTBE, and 50 mg of sodium hydride (60% in mineral oil) are added. After gas evolution ceases, 600 mg of 5-ethyl-4-iodomethyl-2-(4-trifluoromethylphenyl)oxazole are added, and the suspension is heated under reflux overnight. After addition of water and MTBE, the phases are separated, and the organic phase is washed with saturated sodium chloride solution, dried over MgSO4 and concentrated. The residue is purified by preparative HPLC, resulting in 190 mg of tertbutyl 2-{(1S,3R)-3-[5-ethyl-2-(4-trifluoromethylphenyl)oxazol-4-ylmethoxymethyl]-cyclohexylmethoxy}-2-methylpropionate as yellow oil.

$C_{29}H_{40}F_3NO_5$ (539.64): LCMS (ESI): 540.7 [MH⁺].

j) Preparation of 2-{(1S,3R)-3-[5-Ethyl-2-(4-trifluoromethylphenyl)oxazol-4-ylmethoxymethyl]cyclohexylmethoxy}-2-methylpropionic acid

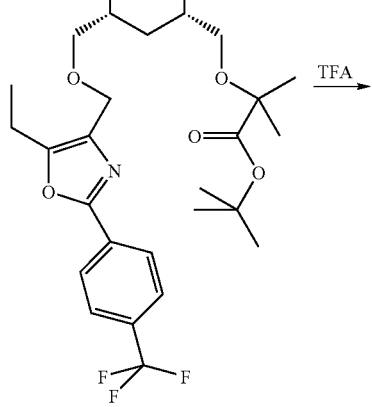

270 mg of tert-butyl 2-{(1S,3R)-3-[5-ethyl-2-(4-trifluoromethylphenyl)oxazol-4-ylmethoxymethyl]cyclohexylmethoxy}-2-methylpropionate are dissolved in 5 ml of dichloromethane and 2.5 ml of trifluoroacetic acid and stirred overnight. The solution is then completely evaporated, and the residue is purified by preparative HPLC, resulting in 127 mg of 2-{(1S,3R)-3-[5-ethyl-2-(4-trifluoromethylphenyl)oxazol-4-ylmethoxymethyl]cyclohexylmethoxy}-2-methylpropionic acid as yellow oil.

$C_{25}H_{32}F_3NO_5$ (483.22): LCMS (ESI): 484.41 [MH⁺].

Example 2 k) Preparation of 2-{(1S,3R)-3-[5-Ethyl-2-(3-trifluoromethylphenyl)-oxazol-4-ylmethoxymethyl]cyclohexylmethoxy}-2-methylpropionic acid

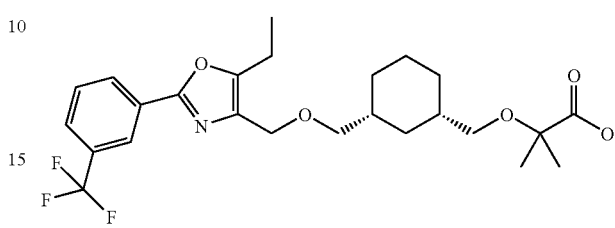

2-{(1S,3R)-3-[5-Ethyl-2-(3-trifluoromethylphenyl)oxazol-4-ylmethoxymethyl]cyclo-hexylmethoxy}-2-methylpropionic acid is obtained in analogy to Example 1 from tert-butyl 2-((1R,3S)-3-hydroxymethylcyclohexylmethoxy)-2-methylpropionate and 5-ethyl-4-iodomethyl-2-(3-trifluoromethylphenyl)oxazole.

$C_{25}H_{32}F_3NO_5$ (483.22): LCMS (ESI): 484.42 [MH⁺].

Example 3 l) Preparation of 2-{(1S,3R)-3-[5-Ethyl-2-(2-trifluoromethylphenyl)-oxazol-4-ylmethoxymethyl]cyclohexylmethoxyl}-2-methylpropionic acid

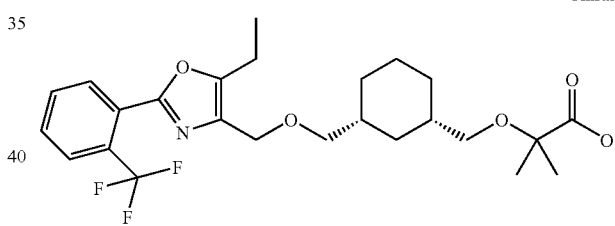

2-{(1S,3R)-3-[5-Ethyl-2-(2-trifluoromethylphenyl)oxazol-4-ylmethoxymethyl]cyclo-hexylmethoxy}-2-methylpropionic acid is obtained in analogy to Example 1 from tert-butyl 2-((1R,3S)-3-hydroxymethylcyclohexylmethoxy)-2-methylpropionate and 5-ethyl-4-iodomethyl-2-(2-trifluoromethylphenyl)oxazole.

$C_{25}H_{32}F_3NO_5$ (483.22): LCMS (ESI): 484.36 [MH⁺].

Example 4 m) Preparation of 2-{(1S,3R)-3-[2-(3,4-Dimethylphenyl)-5-ethyloxazol-4-ylmethoxymethyl]cyclohexylmethoxy}-2-methylpropionic acid

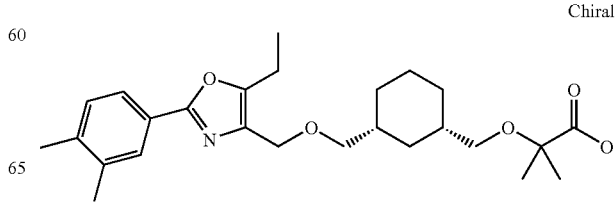

2-{(1S,3R)-3-[2-(3,4-Dimethylphenyl)-5-ethyloxazol-4-ylmethoxymethyl]cyclohexylmethoxy}-2-methylpropionic acid is obtained in analogy to Example 1 from tertbutyl 2-((1R,3S)-3-hydroxymethylcyclohexylmethoxy)-2-methylpropionate and 2-(3,4-dimethylphenyl)-5-ethyl-4-iodomethyloxazole.

$C_{26}H_{37}NO_5$ (443.27): LCMS (ESI): 444.42 [MH$^+$].

Example 5 n) Preparation of 2-{1(1S,3R)-3-[2-(4-tert-butylphenyl)-5-ethyloxazol-4-ylmethoxymethyl]cyclohexylmethoxy}-2-methylpropionic acid

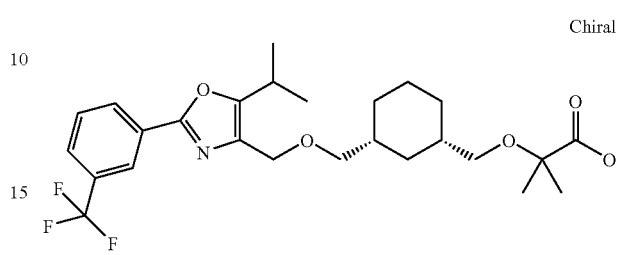

2-{(1S,3R)-3-[2-(4-tert-butylphenyl)-5-ethyloxazol-4-ylmethoxymethyl]cyclo-hexylmethoxy}-2-methylpropionic acid is obtained in analogy to Example 1 from tertbutyl 2-((1R,3S)-3-hydroxymethylcyclohexylmethoxy)-2-methylpropionate and 2-(4-tertbutylphenyl)-5-ethyl-4-iodomethyloxazole.

$C_{28}H_{41}NO_5$ (471.30): LCMS (ESI): 472.46 [MH$^+$].

Example 6 o) Preparation of 2-{(1S,3R)-3-[5-Isopropyl-2-(4-trifluoromethylphenyl)oxazol-4-ylmethoxymethyl]cyclohexylmethoxy}-2-methylpropionic acid

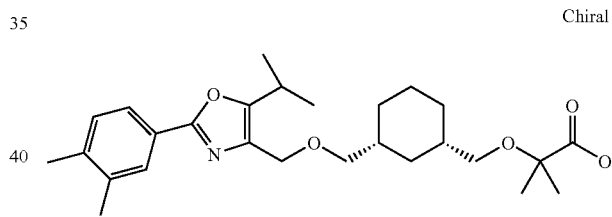

2-{(1S,3R)-3-[5-Isopropyl-2-(4-trifluoromethylphenyl)oxazol-4-ylmethoxymethyl]cyclohexylmethoxy}-2-methylpropionic acid is obtained in analogy to Example 1 from tertbutyl 2-((1R,3S)-3-hydroxymethylcyclohexylmethoxy)-2-methylpropionate and 4-iodomethyl-5-isopropyl-2-(4-trifluoromethylphenyl)oxazole.

C26H34F3NO5 (497.24): LCMS (ESI): 498.41 [MH$^+$].

Example 7 p) Preparation of 2-{(1S,3R)-3-[5-Isopropyl-2-(3-trifluoromethylphenyl)oxazol-4-ylmethoxymethyl]cyclohexylmethoxyl}-2-methylpropionic acid

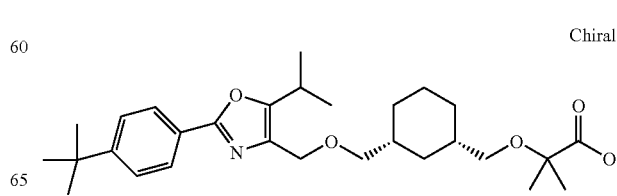

2-{(1S,3R)-3-[5-Isopropyl-2-(3-trifluoromethylphenyl)oxazol-4-ylmethoxymethyl]cyclohexylmethoxy}-2-methylpropionic acid is obtained in analogy to Example 1 from tertbutyl 2-((1R,3S)-3-hydroxymethylcyclohexylmethoxy)-2-methylpropionate and 4-iodomethyl-5-isopropyl-2-(3-trifluoromethylphenyl)oxazole.

$C_{26}H_{34}F_3NO_5$ (497.24): LCMS (ESI): 498.35 [MH$^+$].

Example 8 p) Preparation of 2-{(1S,3R)-3-[2-(3,4-Dimethylphenyl)-5-isopropyloxazol-4-ylmethoxymethyl]cyclohexylmethoxy}-2-methylpropionic acid 2-{(1S,3R)-3-[2-(3,4-Dimethylphenyl)-5-isopropyloxazol-4-ylmethoxymethyl]cyclo-hexylmethoxy}-2-methylpropionic acid is obtained in analogy to Example 1 from tertbutyl 2-((1R,3S)-3-hydroxymethylcyclohexylmethoxy)-2-methylpropionate and 2-(3,4-dimethylphenyl)-4-iodomethyl-5-isopropyloxazole.

$C_{27}H_{39}NO_5$ (457.28): LCMS (ESI): 458.44 [MH$^+$].

Example 9 q) Preparation of 2-{(1S,3R)-3-[2-(4-tert-butylphenyl)-5-isopropyloxazol-4-ylmethoxymethyl]cyclo-hexylmethoxy}-2-methylpropionic acid 2-{(1S,3R)-3-[2-(4-tert-butylphenyl)-5-isopropyloxazol-4-ylmethoxymethyl]cyclohexylmethoxy}-2-methylpropionic acid is obtained in analogy to Example 1 from tert-butyl 2-((1R,3S)-3-hydroxymethylcyclohexylmethoxy)-2-methylpropionate and 2-(4-tert-butylphenyl)-4-iodomethyl-5-isopropyloxazole.

$C_{29}H_{43}NO_5$ (485.31): LCMS (ESI): 486.23 [MH$^+$].

Example 10 r) Preparation of 2-{1(1S,3R)-3-[5-Isopropyl-2-(3-methoxyphenyl)oxazol-4-ylmethoxymethyl]cyclohexylmethoxy}-2-methylpropionic acid Chiral

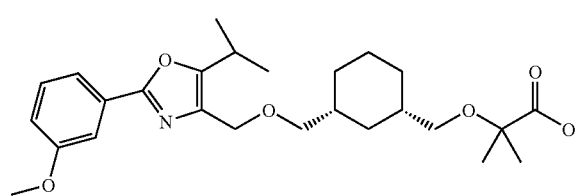

2-{(1S,3R)-3-[5-Isopropyl-2-(3-methoxyphenyl)oxazol-4-ylmethoxymethyl]cyclo-hexylmethoxy}-2-methylpropionic acid is obtained in analogy to Example 1 from tert-butyl 2-((1R,3S)-3-hydroxymethylcyclohexylmethoxy)-2-methylpropionate and 4-iodomethyl-5-isopropyl-2-(3-methoxyphenyl)oxazole.

$C_{26}H_{37}NO_6$ (459.26): LCMS (ESI): 460.42 [MH$^+$].

Example 11 s) Preparation of 2-{(1S,3R)-3-[5-Isopropyl-2-(naphtha-2-yl)oxazol-4-ylmethoxymethyl]cyclohexylmethoxy}-2-methylpropionic acid Chiral

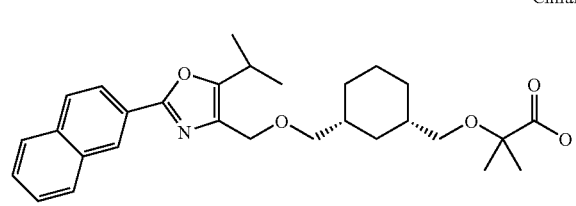

2-{(1S,3R)-3-[5-Isopropyl-2-(naphth-2-yl)oxazol-4-ylmethoxymethyl]cyclo-hexylmethoxy}-2-methylpropionic acid is obtained in analogy to Example 1 from tert-butyl 2-((1R,3S)-3-hydroxymethylcyclohexylmethoxy)-2-methylpropionate and 4-iodomethyl-5-isopropyl-2-(naphth-2-yl)oxazole.

$C_{29}H_{37}NO_5$ (479.27): LCMS (ESI): 480.44 [MH$^+$].

Example 12 s) Preparation of 2-{(1R,3S)-3-[2-(3,4-Dimethylphenyl)-5-isopropyloxazol-4-ylmethoxymethyl]cyclohexylmethoxy}-2-methylpropionic acid

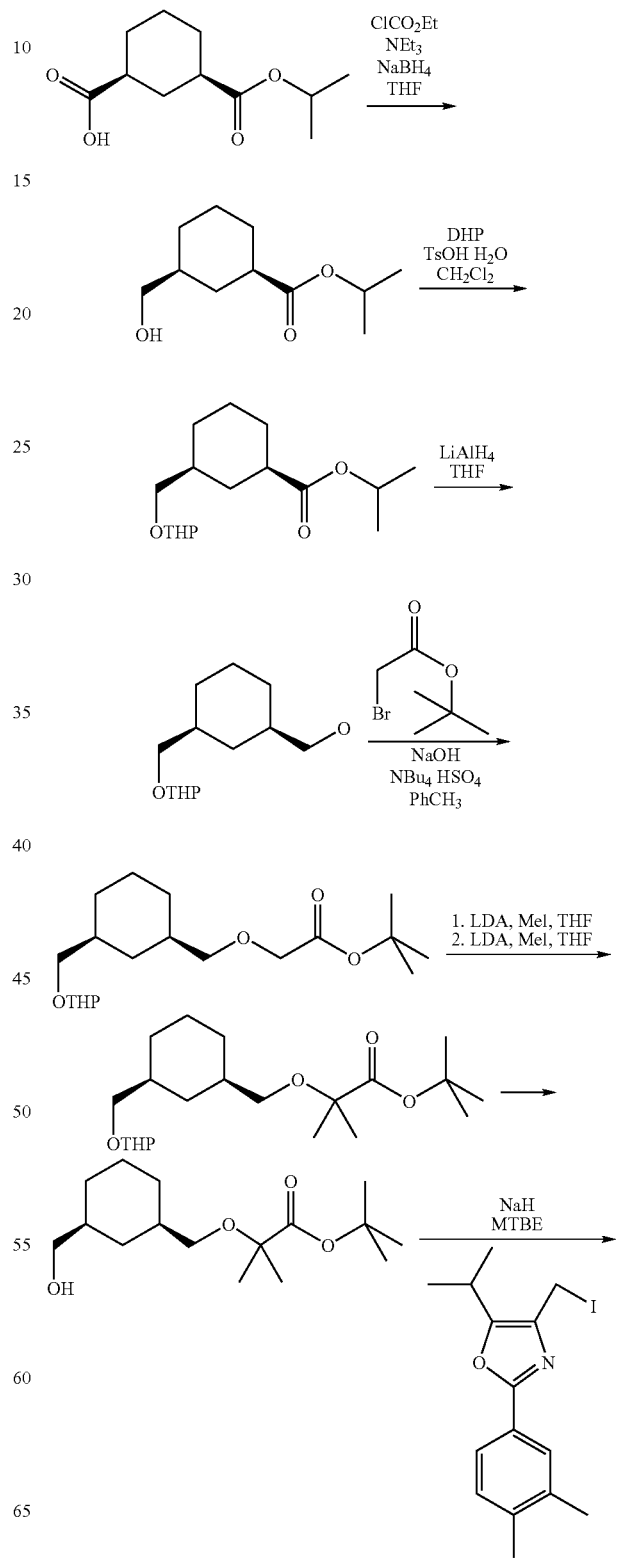

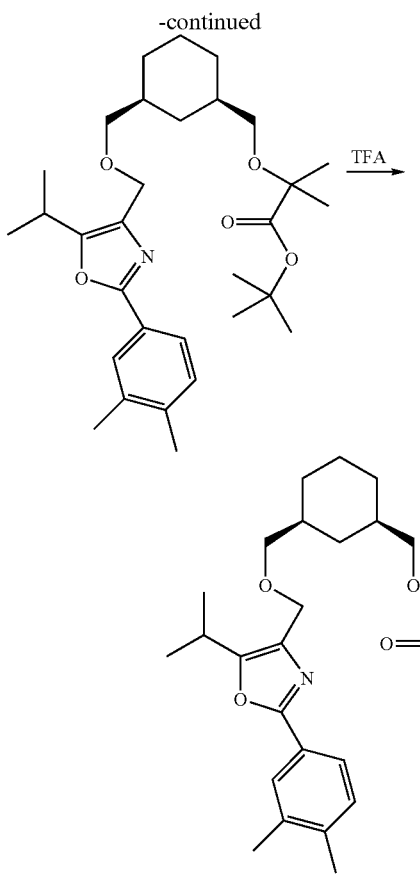

tert-Butyl [(1R,3S)-3-(tetrahydropyran-2-yloxymethyl)cyclohexylmethoxy]acetate

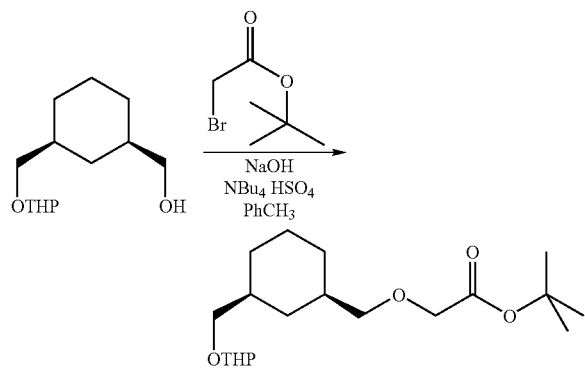

51 g of [(1R,3S)-3-(tetrahydropyran-2-yloxymethyl)cyclohexyl]methanol, 151.5 g tert-butyl bromoacetate, 23.22 g of tetrabutylammonium bisulfate are dissolved in 380 ml of toluene and, at 10° C. (ice-water bath), a solution of 89.36 g of sodium hydroxide in 143 ml of water is added, and the mixture is stirred vigorously (KPG paddle stirrer) at 10° C. and RT for 18 h. Then MTBE and water are added, and the phases are separated. The aqueous phase is extracted twice with MTBE, and the combined organic phases are washed with saturated sodium chloride solution, dried over magnesium sulfate and concentrated. The residue is chromatographed on silica gel (heptane/ethyl acetate gradient). This results in 56.1 g of tert-butyl [(1R,3S)-3-(tetrahydropyran-2-yloxymethyl)cyclohexylmethoxy]acetate as pale yellow oil.

1H-NMR (500 MHz, DMSO): $\square$=4.49-4.53 (m, 1H); 3.91 (s, 2H); 3.67-3.74 (m, 1H); 3.37-3.46 (m, 2H); 3.20-3.27 (m, 2H); 3.09-3.17 (m, 1H); 1.65-1.88 (m, 5H); 1.35-1.62 (m, 7H); 1.15-1.30 (m, 1H); 1.41 (s, 9H); 0.78-0.91 (m, 2H); 0.56-0.68 (m, 1H).

t) Preparation of tert-Butyl 2-methyl-2-[(1R,3S)-3-(tetrahydropyran-2-yloxymethyl)cyclohexyl-methoxy]propionate

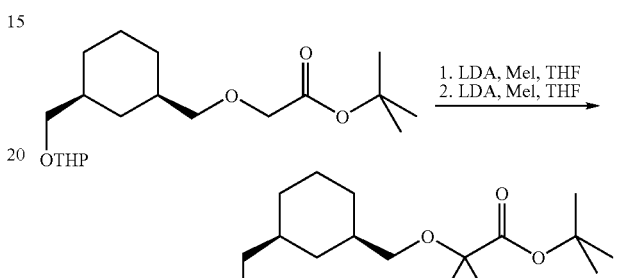

147 ml of a solution of lithium diisopropylamide (2M in THF) are added to a solution of 50.4 g of tert-butyl [(1R,3S)-3-(tetrahydropyran-2-yloxymethyl)cyclohexylmethoxy]-acetate in 450 ml of THF at −78° C., during which the temperature should not rise above −55° C. The solution is stirred at this temperature for 10 min and then warmed to 0° C. and stirred at this temperature for a further 15 min, after which the solution is cooled again to −78° C., and 28.9 ml of methyl iodide are added dropwise. The solution is warmed to 0° C. and then saturated NH4Cl solution and ethyl acetate are added. The phases are separated, the organic phase is washed with saturated NH4Cl solution, the combined aqueous phases are extracted once more with ethyl acetate, and then the combined organic phases are washed with saturated sodium chloride solution, dried over magnesium sulfate and concentrated.

Lithium diisopropylamide (2M in THF) are added to a solution of the residue obtained in this way in 550 ml of THF at −78° C., during which the temperature should not rise above −55° C. The solution is stirred at this temperature for 10 min and then warmed to −10° C. and stirred at this temperature for a further 15 min, after which the solution is again cooled to −78° C., and 34.3 ml of methyl iodide are added dropwise. The solution is warmed to −10° C. and then saturated NH4Cl solution and ethyl acetate are added.

The phases are separated, the organic phase is washed with saturated NH4Cl solution, the combined aqueous phases are extracted once again with ethyl acetate, and then the combined organic phases are washed with saturated sodium chloride solution, dried over magnesium sulfate and concentrated. The residue is chromatographed on silica gel (heptane/ethyl acetate gradient), resulting in 31.4 g of tert-butyl 2-methyl-2-[(1R,3S)-3-(tetrahydropyran-2-yloxymethyl)cyclohexyl-methoxy]-propionate as brown oil.

1H-NMR (500 MHz, DMSO): $\square$=4.49-4.53 (m, 1H); 3.67-3.74 (m, 1H); 3.39-3.46 (m, 2H); 3.05-3.17 (m, 3H); 1.65-1.86 (m, 6H); 1.35-1.62 (m, 6H); 1.41 (s, 9H); 1.15-1.30 (m, 1H); 1.26 (s, 6H); 0.77-0.91 (m, 2H); 0.55-0.67 (m, 1H).

u) Preparation of tert-Butyl 2-((1R,3S)-3-hydroxymethylcyclohexylmethoxy)-2-methylpropionate

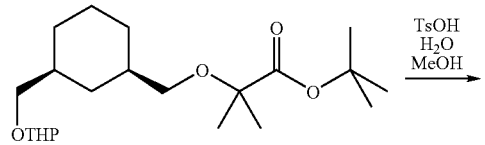

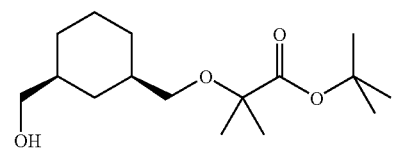

31.4 g of tert-butyl 2-methyl-2-[(1R,3S)-3-(tetrahydropyran-2-yloxymethyl)cyclo-hexylmethoxy]propionate are dissolved in 115 ml of isopropanol and, after addition of 1.61 g of p-toluenesulfonic acid monohydrate, stirred at RT for 78. Subsequently, sat. NaHCO3 solution is added until a neutral reaction is observed with pH paper. The solvent is largely distilled off. The aqueous residue is taken up in water and MTBE.

The aqueous phase is separated off and extracted three times with MTBE. The combined org. phases are washed with water and sat. NaCl solution, dried over MgSO4 and concentrated, and the residue is chromatographed on silica gel (heptane/ethyl acetate 10/1), resulting in 14.9 g of tert-butyl 2-((1R,3S)-3-hydroxymethylcyclohexylmethoxy)-2-methylpropionate as yellow oil.

1H-NMR (500 MHz, DMSO): □=4.32 (t, J=6Hz, 1H); 3.67-3.74 (m, 2H); 3.05-3.12 (m, 2H); 1.76-1.83 (m, 1H); 1.66-1.75 (m, 2H); 1.15-1.50 (m, 4H); 1.41 (s, 9H); 1.27 (s, 6H); 0.71-0.88 (m, 2H); 0.48-0.57 (m, 1H).

v) Preparation of 2-{(1R,3S)-3-[5-Isopropyl-2-(3-trifluoromethylphenyl)oxazol-4-ylmethoxymethyl]cyclohexylmethoxy}-2-methylpropionic acid

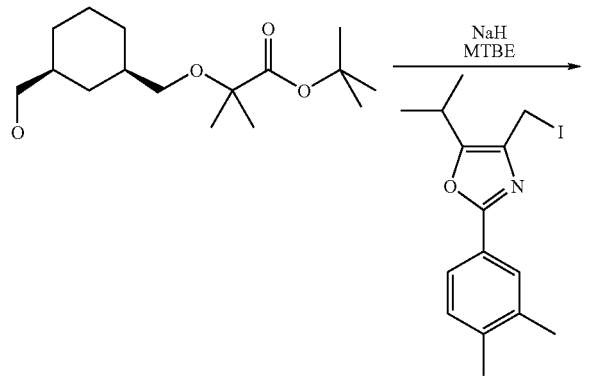

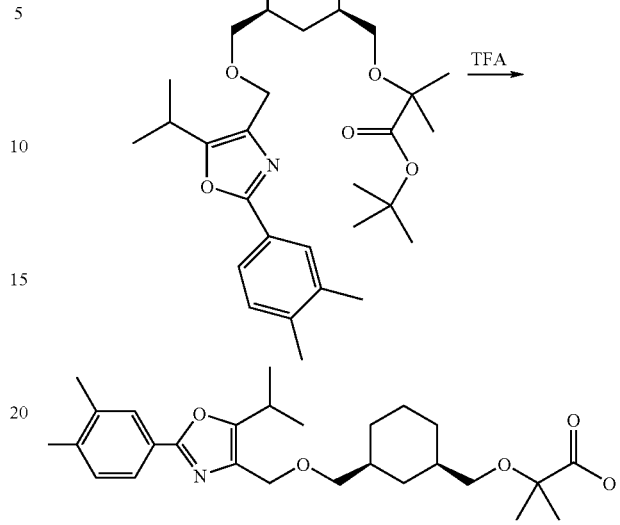

100 mg of tert-butyl 2-((1R,3S)-3-hydroxymethylcyclohexylmethoxy)-2-methylpropionate are dissolved in 2 ml of MTBE, and 21 mg of sodium hydride (60% in mineral oil) are added. After gas evolution subsides, 248 mg of 2-(3,4-dimethylphenyl)-4-iodomethyl-5-isopropyloxazole are added, and the solution is heated under reflux overnight. After addition of water, the phases are separated, the org. phase is dried on a kieselguhr cartridge (Separtis) and the filtrate is concentrated. The residue is taken up in CH2Cl2/TFA (3:1) and left to stand overnight. The solution is completely concentrated, and the residue is purified by prep. HPLC, resulting in 31 mg of 2-{(1R,3S)-3-[5-isopropyl-2-(3-trifluoromethylphenyl)oxazol-4-ylmethoxymethyl]cyclohexylmethoxy}-2-methylpropionic acid.

$C_{27}H_{39}NO_5$ (457.62): LCMS (ESI): 458.32 [MH+].

Example 13 w) Preparation of 2-[(1R,3S)-3-(2-Biphenyl-4-yl-5-methyloxazol-4-ylmethoxymethyl)cyclohexylmethoxy]-2-methylpropionic acid

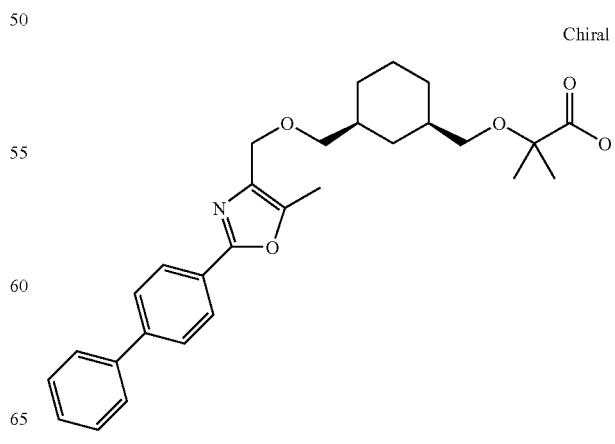

2-[(1R,3S)-3-(2-Biphenyl-4-yl-5-methyloxazol-4-yl-methoxymethyl)cyclohexylmethoxy]-2-methylpropionic acid is obtained in analogy to Example 12 from tert-butyl 2-((1S,3R)-3-hydroxymethylcyclohexylmethoxy)-2-methylpropionate and 2-biphenyl-4-yl-4-iodomethyl-5-methyloxazole.

$C_{29}H_{35}NO_5$ (477.25): LCMS (ESI): 478.30 [MH$^+$].

Example 14 x) Preparation of 2-{(1R,3S)-3-[5-Isopropyl-2-(naphth-2-yl)oxazol-4-ylmethoxymethyl]cyclohexylmethoxy}-2-methylpropionic acid

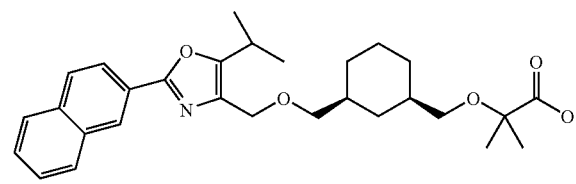

Chiral

2-{(1R,3S)-3-[5-isopropyl-2-(naphth-2-yl)oxazol-4-ylmethoxymethyl]cyclo-hexylmethoxy}-2-methylpropionic acid is obtained in analogy to Example 12 from tert-butyl 2-((1S,3R)-3-hydroxymethylcyclohexylmethoxy)-2-methylpropionate and 4-iodomethyl-5-isopropyl-2-(naphth-2-yl)oxazole.

$C_{29}H_{37}NO_5$ (479.27): LCMS (ESI): 480.30 [MH$^+$].

Example 15 y) Preparation of 2-{(1R,3S)-3-[5-Isopropyl-2-(3-methoxyphenyl)oxazol-4-ylmethoxymethyl]cyclo-hexylmethoxy}-2-methylpropionic acid

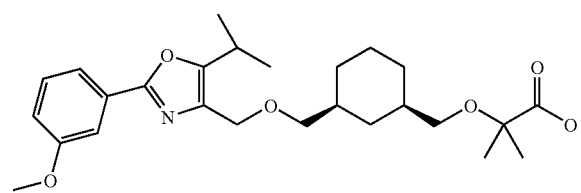

Chiral

2-{(1R,3S)-3-[5-isopropyl-2-(3-methoxyphenyl)oxazol-4-ylmethoxymethyl]cyclo-hexylmethoxy}-2-methylpropionic acid is obtained in analogy to Example 12 from tert-butyl 2-((1S,3R)-3-hydroxymethylcyclohexylmethoxy)-2-methylpropionate and 4-iodomethyl-5-isopropyl-2-(3-methoxyphenyl)oxazole.

$C_{25}H_{35}NO_6$ (445.56): LCMS (ES-): 444.14 [M-H$^+$].

Example 16 z) Preparation of 2-{(1R,3S)-3-[5-Isopropyl-2-(3-trifluoromethylphenyl)oxazol-4-ylmethoxymethyl]cyclohexylmethoxy}-2-methylpropionic acid

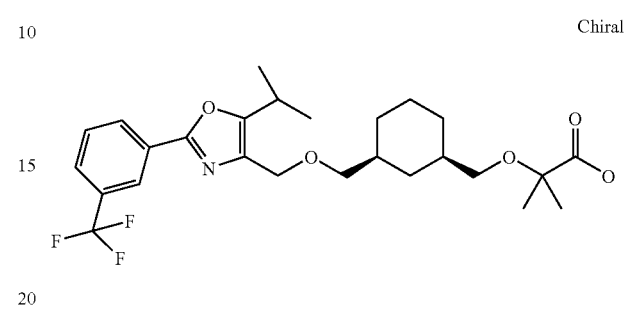

Chiral

2-{(1R,3S)-3-[5-isopropyl-2-(3-trifluoromethylphenyl)oxazol-4-ylmethoxymethyl]cyclo-hexylmethoxy}-2-methylpropionic acid is obtained in analogy to Example 12 from tert-butyl 2-((1S,3R)-3-hydroxymethylcyclohexylmethoxy)-2-methylpropionate and 4-iodomethyl-5-isopropyl-2-(3-trifluoromethylphenyl)oxazole.

$C_{26}H_{34}F_3NO_5$ (497.24): LCMS (ESI): 498.42 [MH$^+$].

Example 17 aa) Preparation of 2-{(1R,3S)-3-[2-(4-Isobutylphenyl)-5-isopropyloxazol-4-ylmethoxymethyl]cyclohexylmethoxy}-2-methylpropionic acid

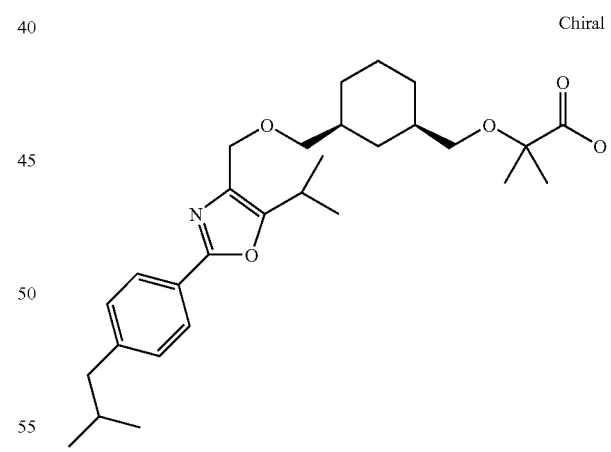

Chiral

2-{(1R,3S)-3-[2-(4-isobutylphenyl)-5-isopropyloxazol-4-ylmethoxymethyl]cyclo-hexylmethoxy}-2-methylpropionic acid is obtained in analogy to Example 12 from tert-butyl 2-((1S,3R)-3-hydroxymethylcyclohexylmethoxy)-2-methylpropionate and 4-iodomethyl-2-(4-isobutylphenyl)-5-isopropyloxazole.

$C_{29}H_{43}NO_5$ (485.67): LCMS (ESI): 486.42 [MH$^+$].

Example 18 bb) Preparation of 2-{(1R,3S)-3-[2-(4-tert-butylphenyl)-5-isopropyloxazol-4-ylmethoxymethyl]cyclohexylmethoxy}-2-methylpropionic acid

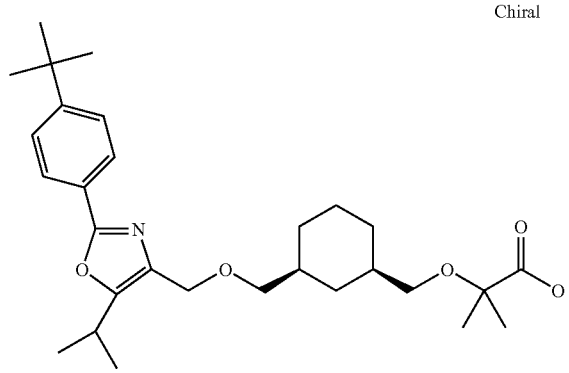

2-{(1R,3S)-3-[2-(4-tert-butylphenyl)-5-isopropyloxazol-4-ylmethoxymethyl]cyclo-hexylmethoxy}-2-methylpropionic acid is obtained in analogy to Example 12 from tert-butyl 2-((1S,3R)-3-hydroxymethylcyclohexylmethoxy)-2-methylpropionate and 4-iodomethyl-2-(4-tert-butylphenyl)-5-isopropyloxazole.

$C_{29}H_{43}NO_5$ (485.67): LCMS (ESI): 486.34 [MH$^+$].

Example 19 cc) Preparation of 2-[(1R,3S)-3-(5-Ethyl-2-naphthalen-2-yl-oxazol-4-ylmethoxymethyl)cyclohexylmethoxy]-2-methylpropionic acid

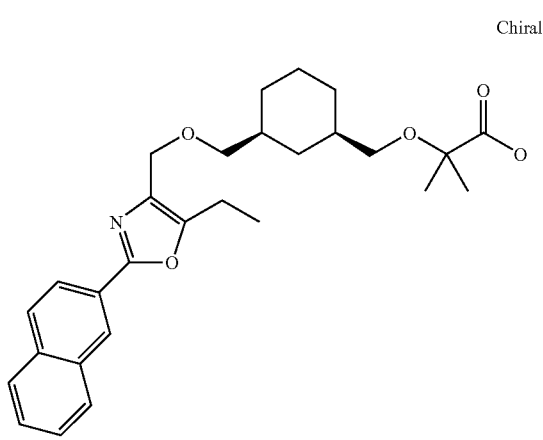

2-[(1R,3S)-3-(5-Ethyl-2-naphthalen-2-yloxazol-4-ylmethoxymethyl)cyclohexylmethoxy]-2-methylpropionic acid is obtained in analogy to Example 12 from tert-butyl 2-((1S,3R)-3-hydroxymethylcyclohexylmethoxy)-2-methylpropionate and 5-ethyl-4-iodomethyl-2-naphthalen-2-yl-oxazole.

$C_{28}H_{35}NO_5$ (465.59): LCMS (ESI): 466.31 [MH$^+$].

Example 20 cc) Preparation of 2-Methyl-2-{(1R,3S)-3-[5-methyl-2-(4-phenoxyphenyl)oxazol-4-ylmethoxymethyl]cyclohexylmethoxy}propionic acid

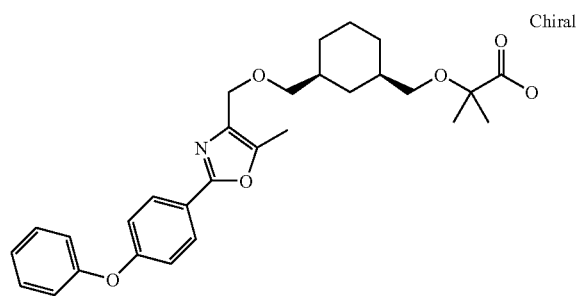

2-Methyl-2-{(1R,3S)-3-[5-methyl-2-(4-phenoxyphenyl)oxazol-4-ylmethoxymethyl]cyclo-hexylmethoxy}propionic acid is obtained in analogy to Example 12 from tert-butyl 2-((1S,3R)-3-hydroxymethylcyclohexylmethoxy)-2-methylpropionate and 4-iodomethyl-5-methyl-2-(4-phenoxyphenyl)oxazole.

$C_{29}H_{35}NO_6$ (493.61): LCMS (ESI): 494.29 [MH$^+$].

Example 21 dd) Preparation of 2-{(1R,3S)-3-[2-(3,4-Dimethylphenyl)-5-ethyloxazol-4-ylmethoxymethyl]cyclohexylmethoxyl}-2-methylpropionic acid

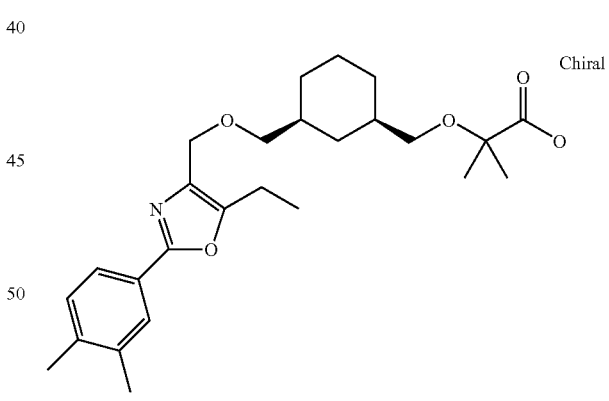

2-{(1R,3S)-3-[2-(3,4-Dimethylphenyl)-5-ethyloxazol-4-ylmethoxymethyl]cyclo-hexylmethoxy}-2-methylpropionic acid is obtained in analogy to Example 12 from tert-butyl 2-((1S,3R)-3-hydroxymethylcyclohexylmethoxy)-2-methylpropionate and 2-(3,4-dimethylphenyl)-5-ethyl-4-iodomethyloxazole.

$C_{26}H_{37}NO_5$ (443.59): LCMS (ES−): 442.20 [M-H$^+$].

What is claimed is:

1. A compound of formula I wherein:
R is H or CF$_3$;
R1 is selected from the group consisting of H, CF$_3$, and (C1-C6)alkyl;
R2 is selected from the group consisting of H, C1-C4 alkyl, O—(C1-C4)-alkyl and CF$_3$;
or
R1 and R2 are fused together with the phenyl ring to comprise naphthyl;
R3 is ethyl or propyl;
R4 is selected from the group consisting of (C1-C6)-alkyl and benzyl; and
R5 is selected from the group consisting of H and (C1-C6)-alkyl;
provided that the compound of formula I is not 2-[cis-3-(5-ethyl-2-(3-methoxyphenyl)oxazol-4-ylmethoxymethyl)cyclohexylmethoxy]-2-methylpropionic acid;
2-[cis-3-(5-ethyl-2-p-isopropyloxazol-4-ylmethoxymethyl)cyclohexylmethoxy]-2-methylpropionic acid;
2-[cis-3-(5-ethyl-2-(2-naphthyl)oxazol-4-ylmethoxymethyl)cyclohexyl methoxy]-2-methylpropionic acid;
2-[cis-3-(5-ethyl-2-p-tolyloxazol-4-ylmethoxymethyl)cyclohexylmethoxy]-2-methylpropionic acid; or
2-[cis-3-(5-ethyl-2-(3-trifluoromethyl)oxazol-4-yl-methoxymethyl)cyclohexylmethoxy]-2-methylpropionic acid;
or a suitable salt, thereof.

2. The compound according to claim 1, wherein
R is H;
R1 is selected from the group consisting of H, methyl, butyl, phenyl, phenoxy and CF$_3$;
R$_2$ is selected from the group consisting of H, methyl, methoxy and CF$_3$;
or
R1 and R2 are fused together with the phenyl ring to comprise naphthyl;
R4 is methyl; and
R5 is H,
or a suitable salt thereof.

3. A pharmaceutical composition comprising at least one compound according to claim 2, or a pharmaceutically acceptable salt thereof, in combination with a pharmaceutically acceptable carrier.

4. The pharmaceutical composition according to claim 3 further comprising at least one anti-diabetic agent.

5. The pharmaceutical composition according to claim 3 further comprising at least one lipid modulator.

6. A pharmaceutical composition comprising at least one compound according to claim 1 or a pharmaceutically acceptable salt thereof in combination with a pharmaceutically acceptable carrier.

7. The pharmaceutical composition according to claim 6 further comprising at least one anti-diabetic agent.

8. The pharmaceutical composition according to claim 6 further comprising at least one lipid modulator.

* * * * *